US012611087B2

(12) United States Patent
Lee

(10) Patent No.: US 12,611,087 B2
(45) Date of Patent: Apr. 28, 2026

(54) DATA PROCESSING DEVICE, SCANNER, AND METHOD FOR OPERATING SAME

(71) Applicant: MEDIT CORP., Seoul (KR)

(72) Inventor: Dong Hoon Lee, Seoul (KR)

(73) Assignee: MEDIT CORP., Seoul (KR)

( * ) Notice: Subject to any disclaimer, the term of this patent is extended or adjusted under 35 U.S.C. 154(b) by 277 days.

(21) Appl. No.: 18/285,694

(22) PCT Filed: Apr. 6, 2022

(86) PCT No.: PCT/KR2022/004974
§ 371 (c)(1),
(2) Date: Oct. 5, 2023

(87) PCT Pub. No.: WO2022/216056
PCT Pub. Date: Oct. 13, 2022

(65) Prior Publication Data
US 2024/0180397 A1 Jun. 6, 2024

(30) Foreign Application Priority Data

Apr. 7, 2021 (KR) ........................ 10-2021-0045438
Oct. 5, 2021 (KR) ........................ 10-2021-0131884

(51) Int. Cl.
*H04N 13/02* (2006.01)
*A61B 1/00* (2006.01)
*A61B 1/24* (2006.01)

(52) U.S. Cl.
CPC ........ *A61B 1/0004* (2022.02); *A61B 1/00006* (2013.01); *A61B 1/0005* (2013.01); *A61B 1/00172* (2013.01); *A61B 1/24* (2013.01)

(58) Field of Classification Search
CPC . A61B 1/0004; A61B 1/00006; A61B 1/0005; A61B 1/00172; A61B 1/24;
(Continued)

(56) References Cited

U.S. PATENT DOCUMENTS

2009/0248184 A1* 10/2009 Steingart ................ A61C 1/084
700/98
2013/0257718 A1* 10/2013 Ojelund .................. G06F 3/011
345/156
(Continued)

FOREIGN PATENT DOCUMENTS

KR 10-2010-0126700 A 12/2010
KR 10-2017-0113412 A 10/2017
(Continued)

OTHER PUBLICATIONS

International Search Report for PCT/KR2022/004974 dated Jul. 8, 2022.
(Continued)

*Primary Examiner* — Howard D Brown, Jr.
(74) *Attorney, Agent, or Firm* — Sughrue Mion, PLLC

(57) ABSTRACT

Provided are a data processing device, a scanner, operating methods thereof, and computer-readable storage media having stored thereon programs for performing the operating methods. The data processing device includes a display, a communication interface, a memory storing one or more instructions, and a processor configured to execute the one or more instructions to control the communication interface to receive, from a scanner, scan data of an object obtained by scanning the object, control the display to display an image corresponding to three-dimensional data generated based on the scan data, while the image is displayed, control the communication interface to receive, from the scanner, a control signal generated according to a user input detected through one or more user interfaces of the scanner, perform a function of adjusting the generated three-dimensional data according to the control signal, and control the display to display the image, based on the adjusted three-dimensional data.

15 Claims, 13 Drawing Sheets

(58) Field of Classification Search
CPC ... A61B 5/0013; A61B 5/0088; A61B 5/0068;
A61B 5/748; A61B 5/0062; G06F
3/04815; G06F 3/0484; G06F 3/0487;
H04N 1/00392; H04N 1/00827; G16H
30/40; G16H 50/50; A61C 9/004; A61C
9/0046; A61C 9/0053; G06T 2210/41;
G06T 2219/2021; G06T 17/00; G06T
19/20
See application file for complete search history.

(56) References Cited

U.S. PATENT DOCUMENTS

| | | | | |
|---|---|---|---|---|
| 2017/0024925 A1* | 1/2017 | Palmer | .................... | G06T 19/20 |
| 2017/0289523 A1* | 10/2017 | Lee | ...................... | H04N 13/207 |
| 2019/0011996 A1* | 1/2019 | Sabina | ................ | G06F 3/04883 |
| 2019/0015177 A1* | 1/2019 | Elazar | .................. | A61C 9/0046 |

FOREIGN PATENT DOCUMENTS

| | | |
|---|---|---|
| KR | 10-2017-0125924 A | 11/2017 |
| KR | 10-2018-0126166 A | 11/2018 |
| WO | 2016/142818 A1 | 9/2016 |

OTHER PUBLICATIONS

Written Opinion for PCT/KR2022/004974 dated Jul. 8, 2022.
Korean Office Action for Korean Application No. 10-2021-0131884 dated Jun. 20, 2023, 18 pages.
Anon: "Intraoral Scanner i500", Functional Manual, Feb. 2019, XP093246420, pp. 1-53.
Extended European Search Report dated Feb. 21, 2025, issued in European Application No. 22784965.0.

* cited by examiner

FIG. 3

USER INPUT–FUNCTION MAPPING INFORMATION — 300

| USER INTERFACE | USER INPUT | FUNCTION |
|---|---|---|
| FIRST SENSOR | FIRST USER INPUT | FIRST FUNCTION |
| | SECOND USER INPUT | SECOND FUNCTION |
| | THIRD USER INPUT | THIRD FUNCTION |
| SECOND SENSOR | FOURTH USER INPUT | FOURTH FUNCTION |
| | FIFTH USER INPUT | FIFTH FUNCTION |
| BUTTON | SIXTH USER INPUT | SIXTH FUNCTION |
| | SEVENTH USER INPUT | SEVENTH FUNCTION |

310

(EX)

| USER INTERFACE | USER INPUT | FUNCTION |
|---|---|---|
| GYRO SENSOR | MOTION OF SHAKING ONE TIME | UNDO |
| | MOTION OF SHAKING TWO TIMES | UNDO |
| | MOTION OF PLACING SCANNER IN CERTAIN ANGLE | LOCKING |
| ACCELERATION SENSOR | TAP ONE TIME | CHANGE SCAN RESOLUTION |
| | TAP TWO TIMES | CHANGE SCAN DEPTH |
| BUTTON | PUSH ONE TIME | CHANGE SCAN LIGHT SOURCE COLOR |
| | PUSH TWO TIMES | CHANGE FILTERING SETTINGS |

DATA PROCESSING DEVICE, SCANNER, AND METHOD FOR OPERATING SAME

CROSS REFERENCE TO RELATED APPLICATIONS

This application is a National Stage of International Application No. PCT/KR2022/004974 filed Apr. 6, 2022, claiming priority based on Korean Patent Application No. 10-2021-0045438 filed Apr. 7, 2021 and Korean Patent Application No. 10-2021-0131884 filed Oct. 5, 2021.

TECHNICAL FIELD

Disclosed embodiments relate to a data processing device, a scanner, and operating methods thereof. More particularly, disclosed embodiments relate to a data processing device, a scanner, and operating methods thereof, for more conveniently controlling processing of image data obtained by a scanner or adjusting of settings of a scanner.

BACKGROUND ART

Recently, as a method of obtaining oral cavity information of a patient, an intraoral scanner that is inserted into the oral cavity of a patient to obtain an image of the inside of the oral cavity is being used. By scanning the oral cavity of a patient by using an intraoral scanner, maxilla scan data, mandible scan data, and occlusion scan data of the maxilla and the mandible may be obtained. A three-dimensional virtual model may be generated by using obtained scan data, and dental treatment or orthodontics may be performed by using the generated three-dimensional virtual model.

A user using an intraoral scanner may identify data obtained by using the intraoral scanner through a display of a data processing device. Also, the user may identify the data displayed on the display and delete the data when the data is unnecessary or incorrect, and scan the oral cavity again. At this time, when the user edits the data, such as by deleting the data, the data may be deleted by using a separate external input device, such as a mouse or a keyboard, for inputting data into the data processing device. During such processes, the user needs to alternately use the intraoral scanner and the external input device, which may lead to a hygienic issue, and work efficiency may decrease due to an increase in movements between a scan operation and a data adjustment operation.

DISCLOSURE

Technical Problem

Disclosed embodiments are to provide a scanner, a data processing device, and operating methods thereof, wherein a function of adjusting data obtained through the scanner, by using the scanner without having to use a separate external input device, is provided.

Disclosed embodiments are to provide a scanner and an operating method thereof, wherein a function of changing settings of the scanner without having to use a separate external input device is provided.

Technical Solution

A data processing device according to an embodiment includes a display, a communication interface, a memory storing one or more instructions, and a processor configured to execute the one or more instructions to control the communication interface to receive, from a scanner, scan data of an object obtained by scanning the object, control the display to display an image corresponding to three-dimensional data generated based on the scan data, control the communication interface to receive, from the scanner, a control signal generated according to a user input detected through one or more user interfaces of the scanner, while the image is displayed, perform a function of adjusting the generated three-dimensional data according to the control signal, and control the display to display the image, based on the adjusted three-dimensional data.

According to an embodiment, the processor may be further configured to execute the one or more instructions to, based on the control signal corresponding to an undo command, hide a predefined number of frames that are most recently input from among frames constituting the three-dimensional data.

According to an embodiment, the processor may be further configured to execute the one or more instructions to, based on the control signal corresponding to a redo command, restore the predefined number of frames that are most recently hidden.

According to an embodiment, the processor may be further configured to execute the one or more instructions to, based on the control signal corresponding to a locking command, finalize the three-dimensional data, based on the three-dimensional data in a current state, such that the hiding or restoring is no longer allowed.

The three-dimensional data may include at least one of voxel data generated based on the scan data and mesh data generated based on the scan data.

According to an embodiment, the processor may be further configured to execute the one or more instructions to control the display to display, on a sub screen, a first image corresponding to first three-dimensional data generated based on scan data corresponding to a first region of the object, control the display to display, on a main screen, a second image corresponding to second three-dimensional data generated based on scan data corresponding to a second region of the object, the second region being spaced apart from the first region, perform a function of adjusting the second three-dimensional data corresponding to the second image displayed on the main screen, according to a control signal received from the scanner, and control the display to display the second image, based on the adjusted second three-dimensional data.

According to an embodiment, the processor may be further configured to execute the one or more instructions to set a locking function on the first three-dimensional data corresponding to the first image displayed on the sub screen, the locking function ensuring that a data adjustment function is not performed.

According to an embodiment, the processor may be further configured to execute the one or more instructions to, when all pieces of the second three-dimensional data are hidden according to an operation of hiding a predefined number of frames that are most recently input from among frames constituting the second three-dimensional data, based on the control signal corresponding to an undo command, control the display to display, on the main screen, the first image corresponding to the first three-dimensional data, the first image corresponding to the sub screen.

A scanner according to an embodiment includes an optical unit performing a scan operation, one or more sensors, a communication interface, and a processor, wherein the processor is configured to control the communication interface to transmit, to a data processing device, scan data of an object obtained by scanning the object by using the optical unit, obtain a user input detected through the one or more sensors, control the optical unit to stop the scan operation according to the user input, and perform a function corresponding to the user input or control the communication interface to transmit, to the data processing device, a control signal instructing the data processing device to perform the function corresponding to the user input.

According to an embodiment, each of the one or more sensors may correspond to one or more functions from among a plurality of functions.

According to an embodiment, the plurality of functions may include at least one of a data adjustment function, a locking function, and a function of adjusting settings of the optical unit.

An operating method of a data processing device, according to an embodiment, includes receiving, from a scanner, scan data of an object obtained by scanning the object, displaying an image corresponding to three-dimensional data generated based on the scan data, while the image is displayed, receiving, from the scanner, a control signal generated according to a user input detected through one or more user interfaces of the scanner, performing a function of adjusting the generated three-dimensional data, according to the control signal, and displaying the image, based on the adjusted three-dimensional data.

An operating method of a scanner including an optical unit and one or more sensors, according to an embodiment, includes transmitting, to a data processing device, scan data of an object obtained by scanning the object by using the optical unit, obtaining a user input detected through the one or more sensors, controlling the optical unit to stop the scanning according to the user input, and performing a function corresponding to the user input or transmitting, to the data processing device, a control signal controlling the data processing device to perform the function corresponding to the user input.

A computer-readable recording medium has recorded thereon one or more programs executed by a processor of a data processing device to implement an operating method of the data processing device, according to an embodiment, wherein the operating method of the data processing device includes receiving, from a scanner, scan data of an object obtained by scanning the object, displaying an image corresponding to three-dimensional data generated based on the scan data, while the image is displayed, receiving, from the scanner, a control signal generated according to a user input detected through one or more user interfaces of the scanner, performing a function of adjusting the generated three-dimensional data, according to the control signal, and displaying the image, based on the adjusted three-dimensional data.

Advantageous Effects

When scan data is to be adjusted while scanning an object by using a scanner according to a disclosed embodiment, the scan data can be adjusted by using the scanner scanning the object without having to use a separate user input device.

When settings of a scanner is to be changed while scanning an object by using the scanner according to a disclosed embodiment, the settings of the scanner can be changed by using the scanner scanning the object without having to use a separate user input device.

DESCRIPTION OF DRAWINGS

The present disclosure may be easily understood by a combination of following detailed descriptions and accompanying drawings, and reference numerals refer to structural elements.

FIG. 3 illustrates an example of user input-function mapping information according to an embodiment.

FIG. 11 is a reference diagram for describing an operation by which a data processing device displays an image corresponding to a plurality of regions of an object, according to an embodiment.

MODE FOR INVENTION

Figure 1:
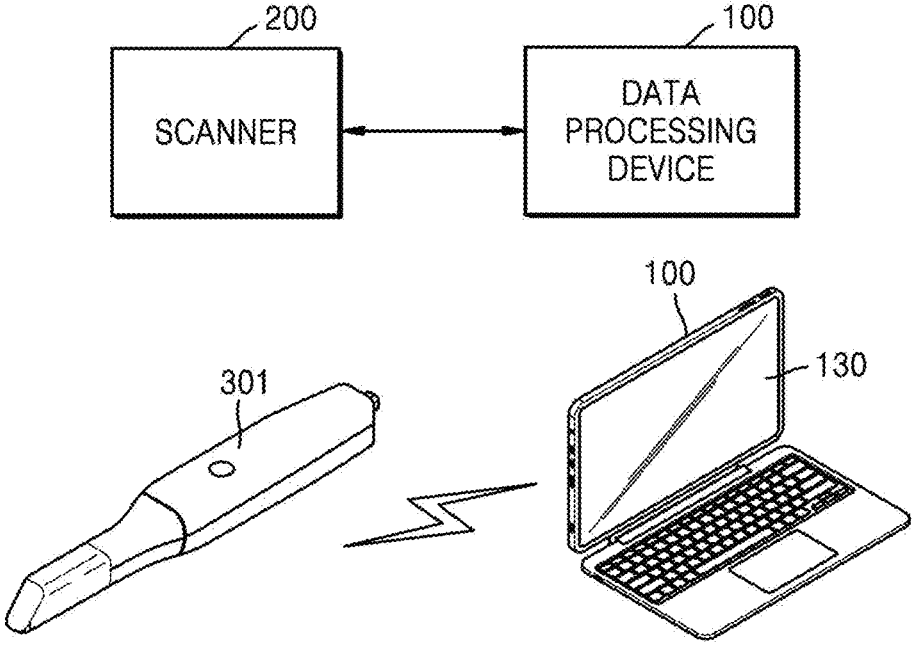
FIG. 1 is a diagram for describing a digital intraoral model processing system according to an embodiment.

The present specification describes the principles of the present disclosure and discloses embodiments such that the scope of right of the present disclosure is clarified and one of ordinary skill in the art may practice the present disclosure. The embodiments may be implemented in various forms.

Throughout the specification, like reference numerals denote like elements. The present specification does not describe all elements of the embodiments, and generic content in the technical field of the present disclosure or redundant content of the embodiments is omitted. The term "part" or "portion" used in the specification may be implemented by software or hardware, and according to embodiments, a plurality of "parts" or "portions" may be implemented as one unit or element, or alternatively, one "part" or "portion" may include a plurality of units or elements. Hereinafter, operation principles and embodiments of the present disclosure will be described with reference to accompanying drawings.

In the present specification, an image may include an image (hereinafter, referred to as an "intraoral image") indicating at least one tooth or an oral cavity including at least one tooth.

Also, in the present specification, an image may include a two-dimensional image of an object or a three-dimensional model or three-dimensional image stereoscopically indicating an object. Also, in the present specification, an image may denote data required to represent an object two-dimensionally or three-dimensionally, for example, raw data obtained from at least one image sensor. In detail, raw data is data obtained to generate an intraoral image and may be data (e.g., two-dimensional data) obtained by at least one image sensor included in an intraoral scanner when the inside of an oral cavity of a patient, which is an object, is scanned by using the intraoral scanner. Raw data obtained by an intraoral scanner may be referred to as scan data or two-dimensional image data.

In the present specification, an object may include a tooth, a gum, at least a partial region of an oral cavity, and/or an artificial structure insertable into an oral cavity (e.g., an orthodontic appliance, an implant, an artificial tooth, or an orthodontic aid inserted into an oral cavity). Here, the orthodontic appliance may include at least one of a bracket, an attachment, an orthodontic screw, a lingual orthodontic appliance, and a removable orthodontic retainer.

Hereinafter, embodiments will be described in detail with reference to accompanying drawings.

FIG. 1 is a diagram for describing a digital intraoral model processing system according to an embodiment.

Referring to FIG. 1, the digital intraoral model processing system may include a scanner 200 and a data processing device 100.

The scanner 200 is a device configured to scan an object. The scanner 200 may include, for example, an intraoral scanner configured to scan a tooth of a patient by being inserted into an oral cavity of the patient, or a model scanner configured to scan a tooth model while moving around the tooth model after setting up the tooth model.

The scanner 200 may use a triangulation technique or a confocal method to measure three-dimensional information of the object. The triangulation technique is a technique of obtaining the three-dimensional information of the object through triangulation by using a triangle formed by a light source, the object to which light emitted from the light source is irradiated, and an image sensor to which light reflected from the object is input. The confocal method is a method of obtaining the three-dimensional information of the object, based on a location of a point determined through the maximum intensity of reflected light, according to a refractive index of a lens transmitting light irradiated to the object.

For example, an intraoral scanner 301 may be a device for obtaining an image of an oral cavity including at least one tooth by being inserted into the oral cavity and scanning the at least one tooth in a non-contact manner. Also, the intraoral scanner 301 may have a shape capable of being introduced into and extracted from the oral cavity, and scans the inside of the oral cavity of the patient by using at least one image sensor (e.g., an optical camera). The intraoral scanner 301 may obtain, as raw data, surface information of the object so as to obtain an image of at least one surface from among a tooth, a gum, and an artificial structure insertable into an oral cavity (e.g., an orthodontic appliance including a bracket and a wire, an implant, an artificial tooth, or an orthodontic aid inserted into an oral cavity), which is the object inside the oral cavity.

Image data obtained by the scanner 200 may be transmitted to the data processing device 100 connected thereto through a communication network wirelessly or via wires.

According to an embodiment, a scanner may transmit, to a data processing device, scan data of an object obtained by scanning the object by using an optical unit.

According to an embodiment, a scanner may obtain a user input detected through one or more sensors provided in the scanner, and control an optical unit to stop a scan operation according to the user input.

According to an embodiment, a scanner may obtain a user input detected through one or more sensors provided in the scanner, and perform a function corresponding to the user input, according to the user input. The function corresponding to the user input may include a function of changing settings of an optical unit provided in the scanner.

According to an embodiment, a scanner may obtain a user input detected through one or more sensors provided in the scanner, and transmit, to a data processing device, a control signal of controlling a function corresponding to the user input to be performed according to the user input. The function corresponding to the user input, which is transmitted to the data processing device, may include a scan data adjustment function. The scan data adjustment function may include scan data undo function, redo function, locking function, and the like.

The data processing device 100 may be any type of electronic device connected to the scanner 200 through a wired or wireless communication network, receiving, from the scanner 200, a two-dimensional image obtained by scanning an oral cavity, and generating, processing, displaying, and/or transmitting an intraoral image, based on the received two-dimensional image.

The data processing device 100 may generate at least one of information generated by processing two-dimensional image data or the intraoral image generated by processing the two-dimensional image data, based on the two-dimensional image data received from the scanner 200, and display the generated information and intraoral image through a display.

The data processing device 100 may be a computing device, such as a smartphone, a laptop computer, a desktop computer, a personal digital assistant (PDA), or a tablet personal computer (PC), but is not limited thereto. Also, the data processing device 100 may be present in the form of a server (or a server device) for processing an intraoral image.

Also, the scanner 200 may transmit, to the data processing device 100, scan data (alternatively referred to as raw data) obtained through scanning. In this case, the data processing device 100 may generate three-dimensional data indicating an oral cavity three-dimensionally, based on the received scan data. "Three-dimensional data" may be generated by three-dimensionally modeling an internal structure of an oral cavity, based on received scan data, and thus may also be referred to as a "three-dimensional intraoral model", a "digital intraoral model", or a "three-dimensional intraoral image".

Also, the data processing device 100 may analyze, process, display, and/or transmit, to an external device, three-dimensional data generated based on the scan data.

As another example, the scanner 200 may obtain the raw data through scanning, generate the three-dimensional data corresponding to the oral cavity of the object by processing the obtained raw data, and transmit the same to the data processing device 100. In this case, the data processing device 100 may analyze, process, display, and/or transmit the received three-dimensional data.

According to an embodiment, the data processing device 100 is an electronic device capable of generating and displaying three-dimensional data indicating an oral cavity including one or more teeth three-dimensionally, and will be described in detail below.

According to an embodiment, upon receiving the scan data obtained by scanning the object from the scanner 200, the data processing device 100 may generate the three-dimensional data by processing the received scan data.

According to an embodiment, the data processing device 100 may receive, from the scanner 200, the scan data of the object obtained by scanning the object.

According to an embodiment, the data processing device 100 may display, in real time, an image corresponding to the three-dimensional data generated based on the scan data received from the scanner 200.

According to an embodiment, the data processing device 100 may, while the image is displayed, receive, from the scanner 200, a control signal generated according to a user input detected through one or more sensors of the scanner 200, perform a function of adjusting the generated three-dimensional data according to the control signal, and display the image by using the adjusted three-dimensional data.

According to an embodiment, based on the control signal corresponding to an undo command, the data processing device 100 may hide a predefined number of frames that are most recently input from among frames constituting the three-dimensional data.

According to an embodiment, based on the control signal corresponding to a redo command, the data processing device 100 may restore the predefined number of frames that are most recently hidden.

According to an embodiment, based on the control signal corresponding to a locking command, the data processing device 100 may finalize the three-dimensional data, based on the three-dimensional data in a current state, such that hiding or restoring is no longer allowed.

According to an embodiment, the data processing device 100 may split a screen of the display into a plurality of screens, and display images corresponding to different regions of the object respectively in the plurality of screens.

According to an embodiment, the data processing device 100 may control the display to display, on a sub screen, a first image corresponding to first three-dimensional data generated based on scan data corresponding to a first region of the object, display, on a main screen, a second image corresponding to second three-dimensional data generated based on scan data corresponding to a second region of the object, which is spaced apart from the first region, perform a function of adjusting the second three-dimensional data corresponding to the second image displayed on the main screen according to a control signal received from the scanner 200, and display the second image by using the adjusted second three-dimensional data.

According to an embodiment, the data processing device 100 may set, on the first three-dimensional data corresponding to the first image displayed on the sub screen, a locking function ensuring that a data adjustment function is not performed.

According to an embodiment, when all pieces of the second three-dimensional data are hidden according to an operation of hiding a predefined number of frames that are most recently input from among frames constituting the second three-dimensional data, based on the control signal corresponding to an undo command, the data processing device 100 may display, on the main screen, the first image corresponding to the first three-dimensional data, which corresponds to the sub screen.

Figure 2:
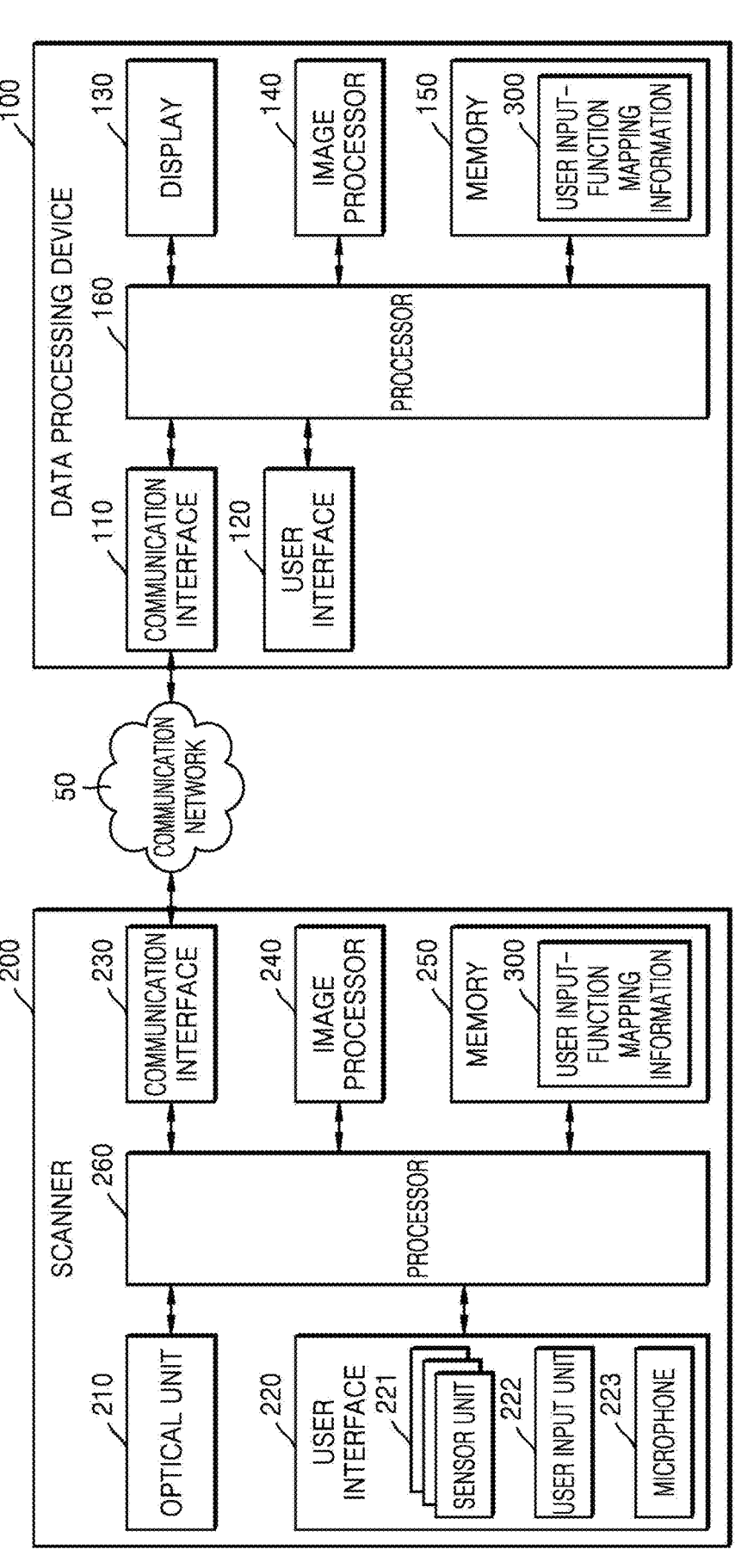
FIG. 2 illustrates an example of a detailed block diagram of a system including a scanner and a data processing device, according to an embodiment.

FIG. 2 illustrates an example of a detailed block diagram of a system including a scanner and a data processing device, according to an embodiment.

Referring to FIG. 2, the system may include the scanner 200, the data processing device 100, and a communication network 50 enabling communication between the scanner 200 and the data processing device 100.

The scanner 200 may transmit, to the data processing device 100 through the communication network 50, two-dimensional scan data obtained by scanning an oral cavity or a tooth cast model of a patient, and the data processing device 100 may generate three-dimensional data by processing the two-dimensional scan data received from the scanner 200 and display, on a display, or transmit, to an external device, an image corresponding to the generated three-dimensional data. Three-dimensional data generated based on scan data may be referred to as a three-dimensional virtual model or a three-dimensional intraoral model.

First, the scanner 200 will be described.

Referring to FIG. 2, the scanner 200 may include an optical unit 210, a user interface 220, a communication interface 230, an image processor 240, a memory 250, and a processor 260.

The optical unit 210 may include a projector projecting light from a light source, and one or more cameras. The optical unit 210 may include, for example, an L camera corresponding to a left field of view and an R camera corresponding to a right field of view, to restore a three-dimensional image according to optical triangulation. The L camera and the R camera may respectively obtain L image data corresponding to the left field of view and R image data corresponding to the right field of view. Raw data including the L image data and the R image data obtained from the optical unit 210 may be transmitted to the processor 260 for data processing.

The user interface 220 may have various modalities to receive a user input of controlling settings of the scanner 200 or controlling adjustment of scan data obtained by the scanner 200.

The user interface 220 may include a sensor unit 221 including one or more sensors for detecting movement of the scanner 200 corresponding to the user input, a user input unit 222, or a microphone 223 receiving a speech of a user.

According to an embodiment, the sensor unit 221 may include a gyro sensor detecting information about the movement of the scanner 200. The gyro sensor may sense information about an operation of the scanner 200, based on x, y, and z axes. For example, when the user performs a scan operation while holding the scanner 200 and then shakes the scanner 200, the gyro sensor may detect the shaking as an input signal. Alternatively, the gyro sensor may detect an input signal according to an angle of the scanner 200 that stopped the scan operation. The sensor unit 221 may detect the number of times the scanner 200 is shook, a specific angle the scanner 200 is positioned, and a motion of a specific pattern performed while holding the scanner 200, as different input signals.

According to an embodiment, the sensor unit 221 may include an acceleration sensor detecting acceleration in a two-axes (x, y) direction or a three-axes (x, y, z) direction. For example, when the user taps the scanner 200, the acceleration sensor may detect the tapping as an input signal. For example, the acceleration sensor may detect different input signals according to the number of times the user taps the scanner 200.

According to an embodiment, the sensor unit 221 may include a touch pad or a touch sensor. For example, when the user touches the touch sensor provided in the scanner 200, the touch sensor may detect the touching as an input signal. The touch sensor may detect different input signals according to a dragging direction, a dragging time, a touching time, or the number of touches.

In addition, the sensor unit 221 may detect rotation, angular displacement, tilt, position, and orientation.

According to an embodiment, the user input unit 222 may include at least one of a keypad, a button, one or more direction buttons or direction keys, a scroll key or jog dial, and a rotation wheel or rotation ring.

When the user input unit 222 includes a hard key button, the user may input a user command of controlling settings of the scanner 200 or controlling adjustment of the scan data obtained by the scanner 200, through a push operation of the hard key button. The user input unit 222 may detect, as different input signals, a type of a button, a number of times a button is pressed, and a duration the button is pressed.

When the user input unit 222 includes a rotation wheel, different input signals may be detected according to the number of times the user rotates the rotation wheel, a rotating direction of the rotation wheel, and a rotating angle of the rotation wheel.

When the user input unit 222 includes one or more direction buttons or direction keys, the one or more direction buttons or direction keys may be detected as different input signals.

In addition, the user input unit 222 may include various types of input units capable of being manipulated by the user, such as a scroll key and a jog key.

The microphone 223 may receive a speech input of the user. The user's speech received by the microphone 223 may be used as a user input by being recognized by a speech recognition device or the like.

The communication interface 230 may communicate with the data processing device 100 through a wired or wireless communication network. In detail, the communication interface 230 may communicate with the data processing device 100 according to control by the processor 260.

In detail, a communication interface may include at least one short-range communication module performing communication according to a communication standard, such as Bluetooth, Wi-Fi, Bluetooth low energy (BLE), NFC/RFID, Wi-Fi direct, UWB, or ZigBee, a long-range communication module performing communication with a server to support long-range communication according to a long-range communication standard, and at least one port to be connected to an external electronic device through a wired cable for wired communication.

The image processor 240 may perform operations for generating and/or processing an image. In detail, the image processor 240 may perform image processing on the two-dimensional image data obtained from the optical unit 210. The image processor 240 may perform, on the two-dimensional image data obtained from the optical unit 210, only processes for data transmission, and output the same to the communication interface 230 for transmission to the data processing device 100.

The memory 250 may store at least one instruction. Also, the memory 250 may store at least one instruction executed by the processor 260. Also, the memory 250 may store at least one program executed by the processor 260. Also, the memory 250 may temporarily store the two-dimensional image data received from the optical unit 210 to transmit the same to the data processing device 100.

According to an embodiment, the memory 250 may store user input-function mapping information 300 defining a function corresponding to a user input received through the user interface 220. The user input-function mapping information 300 may indicate information defining one or more user inputs received through various units, i.e., the sensor unit 221, the user input unit 222, and the microphone 223, included in the user interface 220, and functions corresponding to the respective user inputs. The function corresponding to the user input may largely include at least one of a function of controlling settings of the optical unit 210 of the scanner 200 and a function of controlling the scan data obtained by the scanner 200 to be adjusted by the data processing device 100.

The user input-function mapping information 300 will be described with reference to FIG. 3.

FIG. 3 illustrates an example of the user input-function mapping information 300 according to an embodiment.

Referring to FIG. 3, the user input-function mapping information 300 may include information in which a user input input through each unit of a user interface and a function corresponding thereto are mapped to each other. The user interface may include one or more units of the user interface 220 included in the scanner 200. The user input may indicate a user input which is inputted through a corresponding user interface. The function may define a function performed in response to the user input. The function corresponding to the user input may largely include a function of controlling settings of the optical unit 210 of the scanner 200 and a function of controlling the scan data obtained by the scanner 200 to be adjusted by the data processing device 100. One of ordinary skill in the art would understand that a sensor or button included in the user interface, a user input corresponding thereto, and a corresponding function may be appropriately determined considering a situation of a system.

Referring to FIG. 3, the user input-function mapping information 300 may be information defined such that a first user input through a first sensor is mapped to a first function, a second user input through the first sensor is mapped to a second function, a third user input through the first sensor is mapped to a third function, a fourth user input through a second sensor is mapped to a fourth function, a fifth user input through the second sensor is mapped to a fifth function, a sixth user input through a button is mapped to a sixth function, and a seventh user input through the button is mapped to a seventh function.

Referring to a table 310 showing a specific example of the user input-function mapping information 300, a motion of shaking one time (user input) through a gyro sensor may correspond to an undo function, a motion of shaking two times (user input) through the gyro sensor may correspond to a redo function, a motion of placing a scanner in a certain angle through the gyro sensor may correspond to a locking function, a motion of tapping one time (user input) through an acceleration sensor may correspond to a scan resolution changing function, a motion of tapping two times (user input) through the acceleration sensor may correspond to a scan depth changing function, a motion of pushing one time (user input) through a button may correspond to a scan light source color changing function, and a motion of pushing two times (user input) through the button may correspond to a filtering setting changing function.

FIG. 3 is only an example, and various functions may be mapped in response to user inputs through various sensors.

According to an embodiment, the user input-function mapping information 300 may be stored in the memory 250 while the scanner 200 is manufactured.

According to an embodiment, the user input-function mapping information 300 may be downloaded or updated through a server after the scanner 200 is manufactured or sold.

According to an embodiment, the user input-function mapping information 300 may be customized according to settings by a user. For example, the user input-function mapping information 300 may be transmitted to the scanner 200 after the user customizes settings through the scanner 200 or the data processing device 100 customizes the settings.

The processor 260 may control one or more elements included in the scanner 200 such that an intended operation is performed. Accordingly, even when it is described that the processor 260 performs certain operations, the processor 260 may control at least one element included in the scanner 200 such that the certain operations are performed.

According to an embodiment, the processor 260 may control the optical unit 210 to stop the scan operation when a user input is received from the user interface 220 and detected while scanning the object. For example, when the user wishes to change the settings of the optical unit 210 or adjust the scan data while holding the scanner 200 and scanning the oral cavity of the patient, the user may manipulate the scanner 200 such that the user interface 220 detects the user input. In this case, the processor 260 may control the optical unit 210 to stop the scan operation so as to process the user input received through the user interface 220. The processor 260 may resume the scan operation of the optical unit 210 according to a user input of resuming the scan operation again, after stopping the scan operation of the optical unit 210 and performing the function corresponding to the user input. The user input of resuming the scan operation may be received in any form. For example, the scanner 200 may include a button for toggling between starting and stopping of the scan operation. The processor 260 may resume the scan operation of the optical unit 210 according to reception of the user input of pressing a button provided as such.

According to an embodiment, the processor 260 may identify the function corresponding to the user input received from the user interface 220, by referring to the user input-function mapping information 300 stored in the memory 250.

According to an embodiment, the processor 260 may control the settings of the optical unit 210 according to the user input, when it is determined that the identified function is a function of controlling the settings of the optical unit 210.

According to an embodiment, the function of controlling the settings of the optical unit 210 may include at least one of a scan resolution change, a scan depth change, a scan light source color change, and a filtering setting change.

According to an embodiment, the function of controlling the settings of the optical unit 210 may include the scan resolution change. A scan resolution may include standard definition (SD) and high definition (HD), the scan resolution change may include changing SD to HD or changing HD to SD.

According to an embodiment, the function of controlling the settings of the optical unit 210 may include the scan depth change. A scan depth may indicate a value indicating a distance or depth from a tip portion where the optical unit 210 of the scanner 200 is located to a region to be scanned, during the scan operation of the scanner 200. The scan depth of the scanner 200 may be adjusted in, for example, a range of 12 mm to 21 mm, and an example of a scan depth default value may be 8.5 mm. Such a scan depth may be generally set by using an input device for the data processing device 100, by providing a graphics user interface for changing a scan depth by the data processing device 100. However, according to an embodiment of the present disclosure, the scan depth may be adjusted by using the user interface 220 provided in the scanner 200. For example, when one input signal is repeated by using the user interface 220 of the scanner 200, the scan depth may be changed in the order of 12 mm, 15 mm, 18 mm, and 21 mm. For example, when the user interface 220 includes a gyro sensor and a motion of shaking the scanner 200 one time corresponds to one user input signal, the scan depth may be changed to 12 mm when the scanner 200 is shook one time, changed to 15 mm when the scanner 200 is shook two times, changed to 18 mm when the scanner 200 is shook three times, changed to 21 mm when the scanner 200 is shook four times, and changed back to 12 mm when the scanner 200 is shook five times. Alternatively, the user interface 220 may include two direction keys, and a first direction key may correspond to a change from 12 mm to 15 mm and a second direction key may correspond to a change from 15 mm to 12 mm.

According to an embodiment, the function of controlling the settings of the optical unit 210 may include the scan light source color change. The scan light source color change may include changing a color of a light source of a projector from blue to white or from white to blue.

According to an embodiment, the function of controlling the settings of the optical unit 210 may include the filtering setting change. Filtering settings may include transmitting all pieces of tooth and gum data without filtering the entire oral cavity that is the object, or transmitting only data of a teeth portion after filtering out a gum portion from the obtained scan data.

According to an embodiment, when it is determined that the identified function is the function of processing the scan data by the data processing device 100, the processor 260 may control the communication interface 230 to transmit, to the data processing device 100, a control signal instructing to perform the function of processing the scan data. The function of processing the scan data may include, for example, a function of adjusting the scan data.

To implement embodiments of the present disclosure, the scanner 200 may include only some of the elements shown in FIG. 2, or may include more elements than those shown in FIG. 2.

Referring to FIG. 2, the data processing device 100 may include a communication interface 110, a user interface 120, a display 130, an image processor 140, a memory 150, and a processor 160.

The communication interface 110 may communicate with at least one external electronic device through a wired or wireless communication network. In detail, the communication interface 110 may communicate with the scanner 200 according to control by the processor 160. The communication interface 110 may communicate with an external electronic device or server connected through a wired/wireless communication network according to control by the processor 160.

In particular, the communication interface 10 may include at least one short-range communication module performing communication according to a communication standard, such as Bluetooth, Wi-Fi, BLE, NFC/RFID, Wi-Fi direct, UWB, or ZigBee.

Also, the communication interface 110 may further include a long-range communication module performing communication with a server for supporting long-range communication according to a long-range communication standard. In particular, the communication interface 110 may include the long-range communication module performing communication through a network for Internet communication. Also, the communication interface 110 may include the long-range communication module performing communication through a communication network according to a communication standard, such as 3G, 4G, and/or 5G.

Also, the communication interface 110 may include at least one port to be connected to the external electronic device through a wired cable, to communicate with the external electronic device (e.g., an intraoral scanner) via wires. Accordingly, the communication interface 110 may communicate with the external electronic device connected thereto via wires through the at least one port.

The user interface 120 may receive a user input for controlling the data processing device 100. The user input unit 120 may include a touch panel for detecting a touch of the user, a button for receiving push manipulation of the user, and a user input device including a keyboard or a mouse for designating or selecting one point on a user interface screen, but is not limited thereto.

Also, the user interface 120 may include a speech recognition device for speech recognition. For example, the speech recognition device may be a microphone and may receive the user's speech command or speech request. Accordingly, the processor 160 may control an operation corresponding to the speech command or speech request to be performed.

The display 130 displays a screen. In detail, the display 130 may display a certain screen according to control by the processor 160. In detail, the display 130 may display a user interface screen including an intraoral image generated based on data obtained by scanning an oral cavity of a patient by the scanner 200. Alternatively, the display 130 may display a user interface screen including information related to dental treatment of the patient.

The image processor 140 may perform operations for generating and/or processing an image. In detail, the image processor 140 may receive raw data obtained from the scanner 200 and generate the intraoral image based on the received data. In detail, the image processor 140 may obtain a three-dimensional intraoral model by generating three-dimensional data in a mesh form by processing scan data received from the scanner 200. According to an embodiment, to display, to the user, the scan data received from the scanner 200 in a three-dimensional form by processing the scan data in real time, the image processor 140 may generate voxel data by processing the scan data and display an image corresponding to the generated voxel data on the display 130. Obviously, when a processing performance of the data processing device 100 is satisfied, the data processing device 100 may process the scan data immediately to mesh data and display an image corresponding to the mesh data on the display 130 in real time.

In FIG. 2, the image processor 140 is illustrated as a separate element, but in another example, a program corresponding to an operation performed by the image processor 140 may be stored in the memory 150 and the processor 160 may execute the program stored in the memory 150 to perform an image processing operation.

The memory 150 may store at least one instruction. Also, the memory 150 may store at least one instruction executed by the processor 160. Also, the memory 150 may store at least one program executed by the processor 160. Also, the memory 150 may store data (e.g., the raw data obtained through intraoral scanning) received from the scanner 200. Alternatively, the memory 150 may store an intraoral image three-dimensionally showing an oral cavity.

According to an embodiment, the memory 150 may store a part or all of the user input-function mapping information 300. In detail, the memory 150 may store all of the user input-function mapping information 300 or store only information related to a control function performed by the data processing device 100 from among the user input-function mapping information 300.

The processor 160 performs at least one instruction stored in the memory 150 to control an intended operation to be performed. Here, the at least one instruction may be stored in an internal memory included in the processor 160 or in the memory 150 included in the data processing device 100 separately from the processor 160.

In detail, the processor 160 may perform the at least one instruction to control at least one element included in the data processing device 100 such that an intended operation is performed. Accordingly, even when it is described that the processor 160 performs certain operations, the processor 160 may control at least one element included in the data processing device 100 such that the certain operations are performed.

According to an embodiment, the processor 160 may execute one or more instructions stored in the memory 150 to control the communication interface 110 to receive, from the scanner 200, scan data of an object obtained by scanning the object, control the display 130 to display an image corresponding to three-dimensional data generated based on the scan data, control the communication interface 110 to, while the image is displayed, receive, from the scanner 200, a control signal generated according to a user input detected through one or more user interfaces 220 of the scanner 200, perform a function of adjusting the generated three-dimensional data according to the control signal, and control the display 130 to display the image by using the adjusted three-dimensional data.

According to an embodiment, the processor 160 may execute the one or more instructions stored in the memory 150 to, based on the control signal corresponding to an undo command, hide a predefined number of frames that are most recently input from among frames constituting the three-dimensional data.

According to an embodiment, the processor 160 may execute the one or more instructions stored in the memory 150 to, based on the control signal corresponding to a redo command, restore a predefined number of frames that are most recently hidden.

According to an embodiment, the processor 160 may execute the one or more instructions stored in the memory 150 to, based on the control signal corresponding to a locking command, finalize the three-dimensional data, based on the three-dimensional data in a current state, such that the hiding or restoring is no longer allowed.

According to an embodiment, the processor 160 may execute the one or more instructions stored in the memory 150 to control the display 130 to display, on a sub screen, a first image corresponding to first three-dimensional data generated based on scan data corresponding to a first region of the object, control the display 130 to display, on a main screen, a second image corresponding to second three-dimensional data generated based on scan data corresponding to a second region of the object, the second region being spaced apart from the first region, perform a function of adjusting the second three-dimensional data corresponding to the second image displayed on the main screen, according to a control signal received from the scanner 200, and control the display 130 to display the second image, by using the adjusted second three-dimensional data.

According to an embodiment, the processor 160 may execute the one or more instructions stored in the memory 150 to set a locking function on the first three-dimensional data corresponding to the first image displayed on the sub screen, the locking function ensuring that a data adjustment function is not performed.

According to an embodiment, the processor 160 may execute the one or more instructions stored in the memory 150 to, when all pieces of the second three-dimensional data are hidden according to an operation of hiding a predefined number of frames that are most recently input from among frames constituting the second three-dimensional data, based on the control signal corresponding to an undo command, control the display 130 to display, on the main screen, the first image corresponding to the first three-dimensional data, corresponding to the sub screen.

According to an embodiment, the processor 160 may include therein, at least one internal processor and a memory device (e.g., RAM or ROM) storing at least one of a program, an instruction, a signal, and data to be processed or used by the internal processor.

In addition, the processor 160 may include a graphics processing unit (GPU) for graphic processing corresponding to a video. Also, the processor 160 may be implemented as a system-on-chip (SoC) in which a core and the GPU are integrated. Also, the processor 160 may include a multi-core greater than a single core. For example, the processor 160 may include a dual-core, a triple-core, a quad-core, a hexa-core, an octa-core, a deca-core, a dodeca-core, or hexadeca-core.

According to an embodiment, the processor 160 may generate the intraoral image based on the two-dimensional image data received from the intraoral scanner 301.

In detail, the communication interface 110 may receive data obtained by the intraoral scanner 301, for example, raw data obtained through intraoral scanning, according to control by the processor 160. Also, the processor 160 may generate the three-dimensional intraoral image indicating an oral cavity three-dimensionally, based on the raw data received by the communication interface 110. For example, the intraoral scanner 301 may include an L camera corresponding to a left field of view and an R camera corresponding to a right field of view, to restore the three-dimensional image according to optical triangulation. Also, the intraoral scanner 301 may obtain, from the L camera and the R camera, L image data corresponding to the left field of view and R image data corresponding to the right field of view, respectively. Continuously, the intraoral scanner (not shown) may transmit the raw data including the L image data and the R image data to the communication interface 110 of the data processing device 100.

Then, the communication interface 110 may transmit the received raw data to the processor 160 and the processor 160 may generate the intraoral image showing the oral cavity three-dimensionally, based on the received raw data.

Also, the processor 160 may control the communication interface 110 to directly receive the intraoral image showing the oral cavity three-dimensionally, from an external server, a medical device, or the like. In the case, the processor 160 may obtain the three-dimensional intraoral image without having to generate the three-dimensional intraoral image based on the raw data.

According to an embodiment, the processor 160 performing "extracting", "obtaining", "generating" or the like may indicate not only that the processor 160 directly performs such an operation by executing at least one instruction, but also the processor 160 controls other elements such that the operation is performed.

To implement embodiments of the present disclosure, the data processing device 100 may include only some of the elements shown in FIG. 2, or may include more elements than those shown in FIG. 2.

Also, the data processing device 100 may store and execute dedicated software linked to the scanner 200. Here, the dedicated software may be referred to as a dedicated program, a dedicated tool, or a dedicated application. When the data processing device 100 operates in association with the scanner 200, the dedicated software stored in the data processing device 100 may be connected to the scanner 200 and receive, in real time, pieces of data obtained through the intraoral scanning. For example, Medit i500, which is an intraoral scanner, contains dedicated software for processing data obtained through intraoral scanning. In detail, Medit has produced and is distributing "Medit Link" that is software for processing, managing, using, and/or transmitting data obtained by an intraoral scanner (e.g., 500). Here, the dedicated software denotes a program, tool, or application operable in association with the intraoral scanner, and thus various intraoral scanners developed and sold by various manufacturers may commonly use the dedicated software. Also, the dedicated software may be produced and distributed separately from the intraoral scanner performing intraoral scanning. The data processing device 100 may store and execute the dedicated software corresponding to i500. The dedicated software may perform at least one operation for obtaining, processing, storing, and/or transmitting the intraoral image. Here, the dedicated software may be stored in a processor. Also, the dedicated software may provide a user interface for using data obtained by the intraoral scanner. Here, a user interface screen provided by the dedicated software may include an intraoral image generated according to an embodiment.

Figure 4:
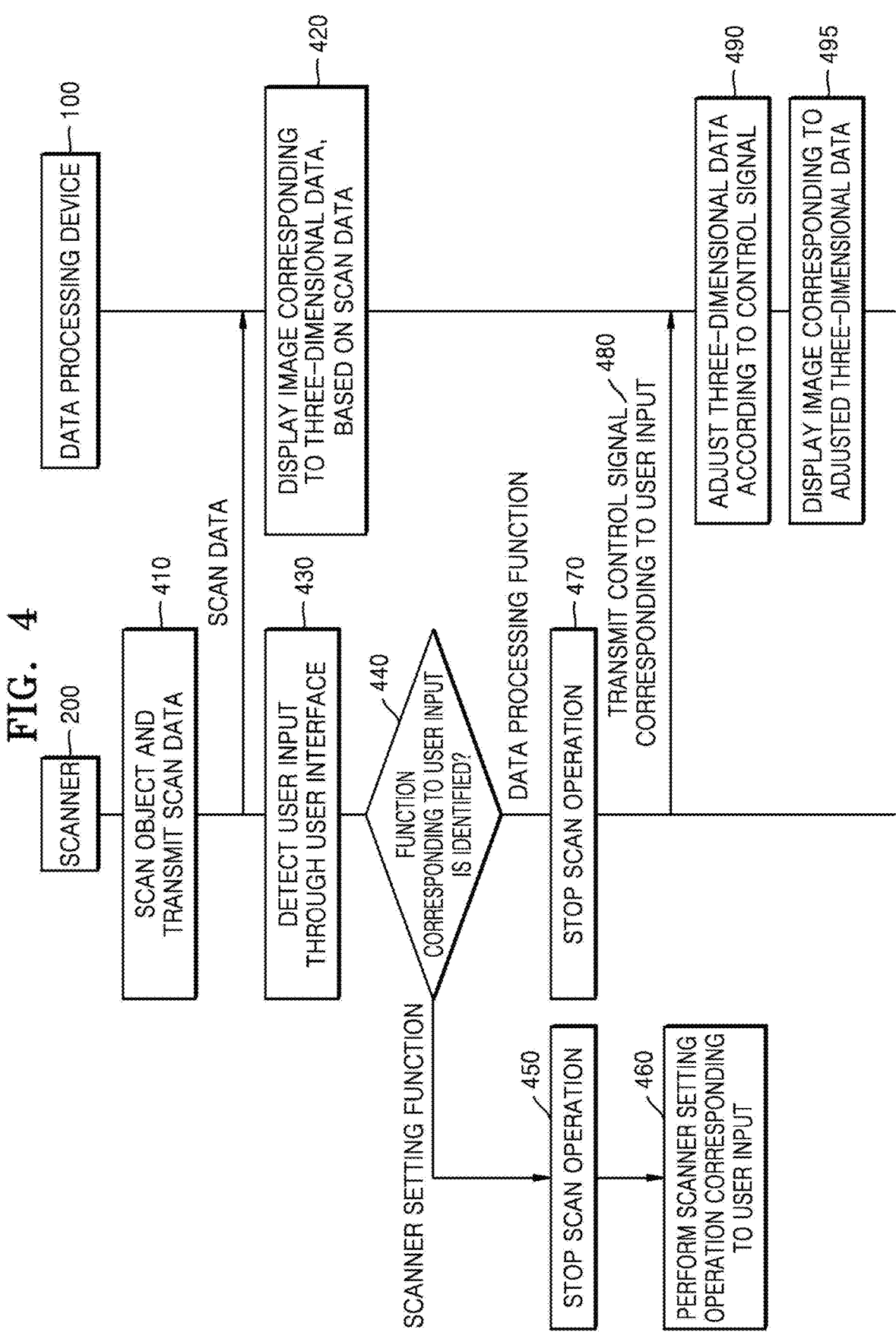
FIG. 4 illustrates an example of a flowchart of operating processes of a scanner and a data processing device, according to an embodiment.

FIG. 4 illustrates an example of a flowchart of operating processes of a scanner and a data processing device, according to an embodiment.

Referring to FIG. 4, in operation 410, the scanner 200 may scan an object and transmit scan data obtained through the scanning to the data processing device 100. The object may be an oral cavity of a patient or a teeth model, but is not limited thereto. The object may be any body part or thing to be scanned. For example, a doctor may scan the oral cavity of the patient by moving the scanner 200 inside the oral cavity of the patient while holding the scanner 200. The scan data may be transmitted to the data processing device 100 in real time.

In operation 420, the data processing device 100 may receive the scan data from the scanner 200 in real time, and display an image corresponding to three-dimensional data, based on the received scan data. In detail, the data processing device 100 may generate the three-dimensional data corresponding to an intraoral model of the patient, based on the scan data received from the scanner 200, and display, on a display, the image corresponding to the generated three-dimensional data. The three-dimensional data may include voxel data or mesh data.

Figure 5:
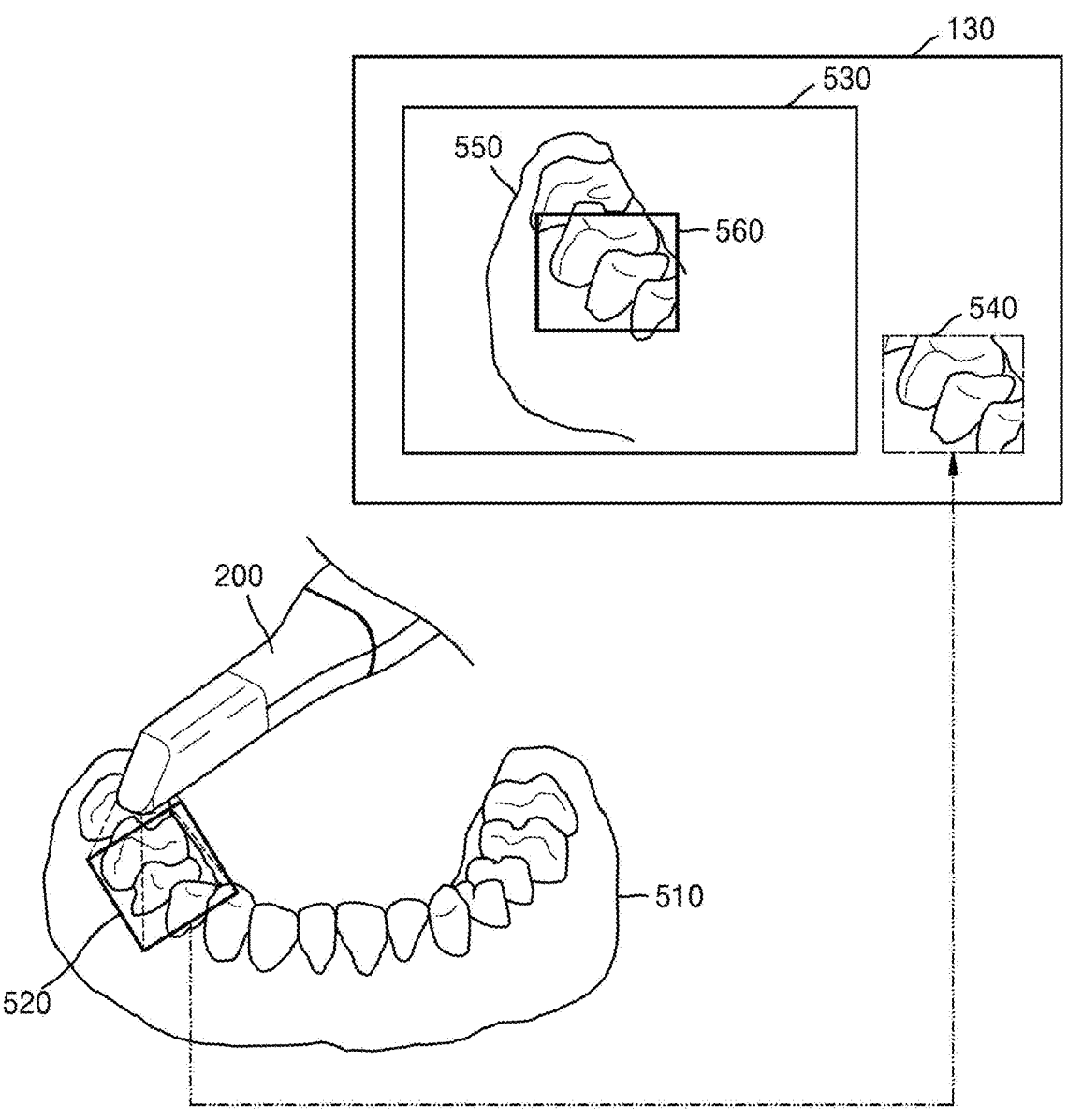
FIG. 5 is a reference diagram for describing a process of displaying, by a data processing device, a three-dimensional virtual model generated by using two-dimensional data obtained through a scanner, according to an embodiment.

FIG. 5 is a reference diagram for describing a process of displaying, by a data processing device, a three-dimensional virtual model generated by using two-dimensional data obtained through a scanner, according to an embodiment.

Referring to FIG. 5, the scanner 200 may project light onto an oral cavity 510 of a patient through a projector, and obtain two-dimensional image data of the oral cavity through one or more cameras. Here, the scanner 200 may project light onto a scan region of interest (ROI) 520, and obtain two-dimensional image data corresponding to the scan ROI 520. Data obtained as the scanner 200 performs scanning while moving along teeth in the oral cavity 510 may be transmitted to the data processing device 100 in real time.

The data processing device 100 may receive the two-dimensional image data corresponding to the scan ROI 520 from the scanner 200 in real time, and generate three-dimensional data by matching the received one or more pieces of two-dimensional image data. Referring to FIG. 5, the data processing device 100 may display data through two windows, i.e., a main window 530 and a sub window 540, on a screen of the display 130. For example, the data processing device 100 may display, in the main window 530 (or a first window), an image corresponding to a three-dimensional virtual model generated by the data processing device 100 and display, on the sub window 540 (or a second window), an image of the three-dimensional data corresponding to the scan ROI 520 currently scanned by the scanner 200.

In other words, the data processing device 100 may display, on the sub window 540, the image corresponding to the three-dimensional data obtained by processing scan data of the scan ROI 520 received from the scanner 200 in real time, generate the three-dimensional virtual model by collecting pieces of the scan data corresponding to the scan ROI 520 received from the scanner 200 in real time, and display, on the main window 530, an image 550 of the generated three-dimensional virtual model. A box 560 for indicating the scan ROI 520 in the three-dimensional virtual model may be displayed on the image 550 of the three-dimensional virtual model in the main window 530.

As shown in FIG. 5, the three-dimensional data corresponding to the image displayed on the main window 530 or sub window 540 of the display 130 may include voxel data and/or mesh data.

Hereinafter, the voxel data and the mesh data will be described with reference to FIG. 6.

Figure 6:
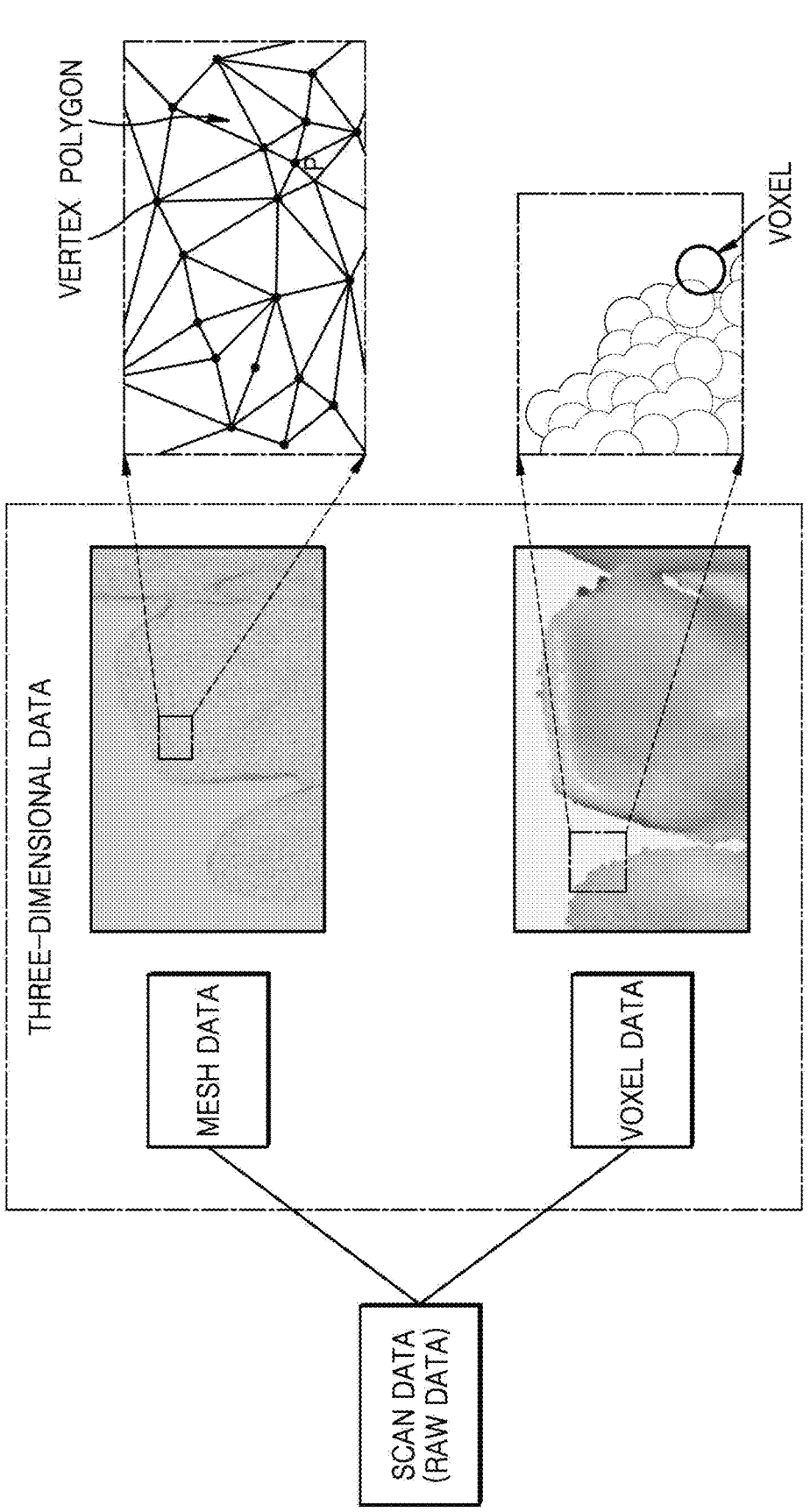
FIG. 6 is a reference diagram for describing voxel data and mesh data, which are processed based on scan data, according to an embodiment.

FIG. 6 is a reference diagram for describing voxel data and mesh data, which are processed based on scan data, according to an embodiment.

The data processing device 100 may receive scan data from the scanner 200, process the scan data, and obtain a three-dimensional virtual model by generating mesh data including a polygon and a vertex. The data processing device 100 may establish and apply a plan for intraoral treatment or orthodontics, based on the three-dimensional virtual model in a mesh form. When two-dimensional data is obtained by using the scanner 200, the data processing device 100 may calculate coordinates of a plurality of illuminated surface points by using triangulation. The coordinates of the surface points may be accumulated as the number of pieces of scan data increases while moving along a surface of an object by using the scanner 200. As a result of obtaining such an image, a point cloud of the vertices may be identified and a range of surfaces may be indicated. The points in the point cloud may indicate points actually measured on a three-dimensional surface of the object. A surface structure may be approximated by forming a polygonal mesh in which adjacent vertices of the point cloud are connected by a line segment. The polygonal mesh may be variously determined to be a triangular, quadrangular, or pentagonal mesh. A relationship between neighboring polygons of a mesh model may be used to extract features of teeth boundaries, for example, a curvature, a minimum curvature, an edge, and a spatial relationship. For example, referring to FIG. 6, three-dimensional data may include a plurality of vertices constituting a point cloud, and a triangular mesh generated by connecting adjacent vertices to each other. Each vertex may include, as its attribute, position information and color information. The position information of each vertex, as an attribute, may include X, Y, and Z coordinates on a three-dimensional coordinate system. The color information of each vertex, as an attribute, may include an RGB value indicating a color obtained by a camera or image sensor included in a scan device. As such, a shape, an outline, and a color of a three-dimensional intraoral model may be represented by the attributes of the vertices, i.e., the position information and the color information.

The data processing device 100 may generate and display the three-dimensional virtual model in the mesh form by receiving the scan data in real time. However, for the data processing device 100 to receive the scan data and process the same into the three-dimensional virtual model in the mesh form in real time, the data processing device 100 requires a high processing speed and high performance. Thus, data displayed by the data processing device 100 on a screen of a display in real time may use voxel data instead of the mesh data.

The data processing device 100 may generate volume data including volume elements (i.e., voxels) that are default data used to represent a 3D object by using the scan data. Generally, a voxel denotes a pixel further including a z-coordinate that is a third coordinate, in addition to an x-coordinate and a y-coordinate in a Cartesian coordinate system. In other words, voxels indicate cubes having a same size forming a 3D space defined discretely. Generally, a voxel-based 3D scene may include one or more voxel sets and each voxel set may include one or more voxels. 3D voxel data is rendered by an appropriate output device, such as a display, to generate a 2D image. The rendering indicates generating a 2D graphics image on the output device from a 3D voxel data file, and includes generating an image by using a color or texture to assign a sense of reality to the image.

Generally, because it is easier to render an image by using voxel data instead of mesh data in real time, in terms of processing speed or processing performance, the data processing device 100 may use the voxel data to display, in real time, an image of scan data received from a scanner.

Referring back to FIG. 4, the data processing device 100 may display, in real time, the image corresponding to the three-dimensional data by using the voxel data or mesh data, based on the scan data, as described above, in operation 420.

In operation 430, the scanner 200 may detect a user input through a user interface while scanning the object. The scanner 200 may detect the user input through one or more sensors included in the user interface, a button, or a microphone.

In operation 440, the scanner 200 may identify a function corresponding to the user input detected through the user interface. In detail, the scanner 200 may store information obtained by matching corresponding functions to various user input detected through the user interface. For example, the scanner 200 may store the user input-function mapping information 300 shown in FIG. 3. Accordingly, when the user input is detected, the scanner 200 may search for a corresponding function by referring to the user input-function mapping information 300 as shown in FIG. 3. The scanner 200 may identify whether the function corresponding to the user input is related to a scanner setting function or a scan data processing function. When it is determined that the function corresponding to the user input corresponds to the scanner setting function, operation 450 may be performed.

In operation 450, the scanner 200 may stop a scan operation.

In operation 460, the scanner 200 may perform a scanner setting operation corresponding to the user input. For example, the scanner 200 may refer to the user input-function mapping information 300 shown in FIG. 3 to identify the scanner setting function corresponding to the detected user input and perform the identified scanner setting function. The scanner setting function is a function of changing settings of a scanner, and for example, may include scan resolution change, a scan depth change, a scan light source color change, and a filtering setting change.

When it is determined that the function corresponding to the user input corresponds to the scan data processing function in operation 440, operation 470 may be performed.

In operation 470, the scanner 200 may stop the scan operation. When the scan operation is stopped, transmitting, in real time, of the scan data may also be stopped.

In operation 480, the scanner 200 may transmit a control signal corresponding to the user input to the data processing device 100. For example, the scanner 200 may refer to the user input-function mapping information 300 shown in FIG. 3 to identify the scan data processing function corresponding to the detected user input and transmit, to the data processing device 100, the control signal instructing to perform the identified scan data processing function. For example, the scan data processing function may include an undo function, a redo function, and a locking function.

In operation 490, the data processing device 100 may receive, from the scanner 200, the control signal corresponding to the user input and process the three-dimensional data according to the received control signal. The processing of the three-dimensional data may include an undo process, a redo process, or a locking process performed on the three-dimensional data corresponding to the image displayed on the display of the data processing device 100.

In operation 495, the data processing device 100 may display the image corresponding to the processed three-dimensional data.

Figure 7:
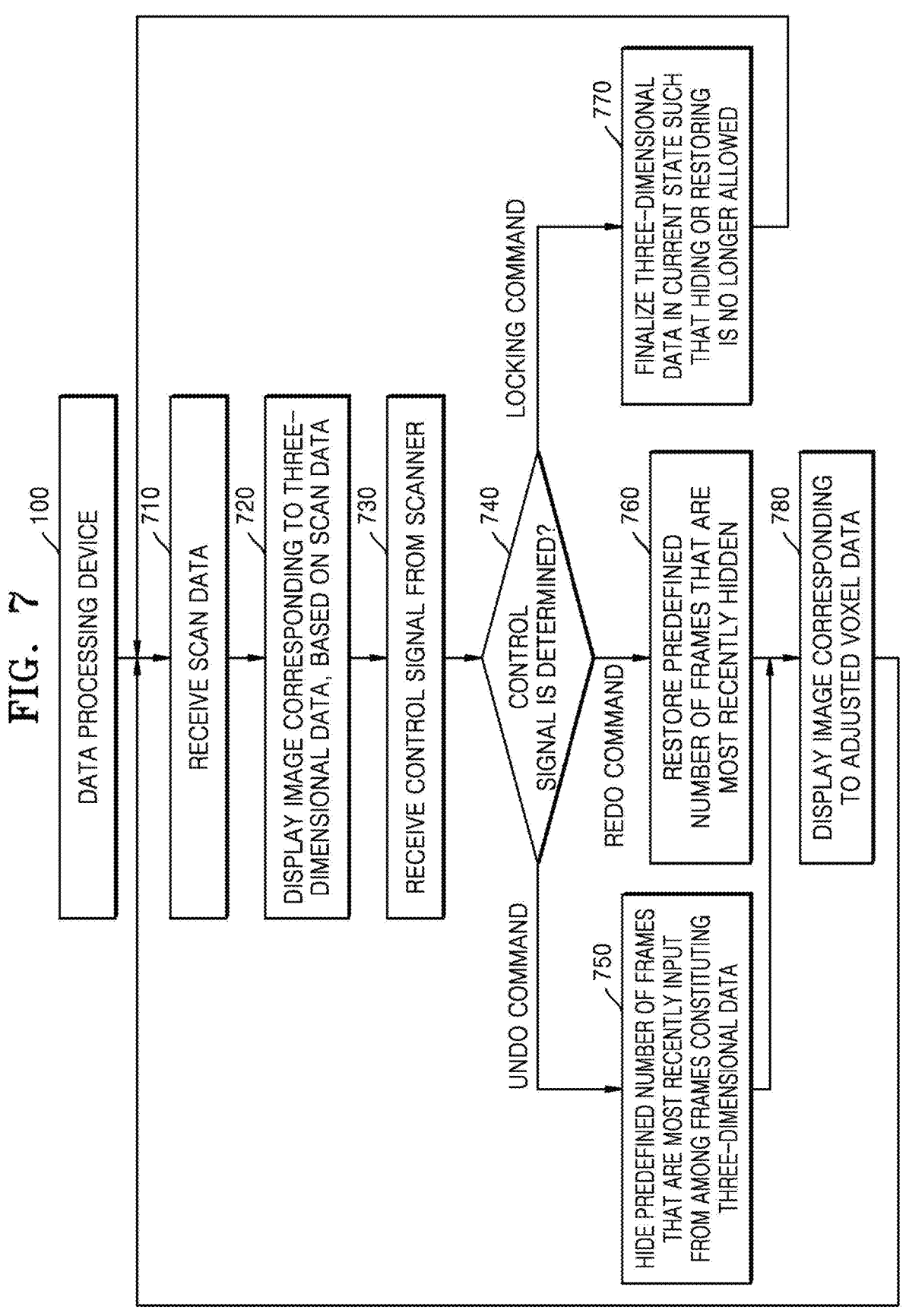
FIG. 7 is a detailed flowchart according to an example of an operating method performed by a data processing device, according to an embodiment.

FIG. 7 is a detailed flowchart according to an example of an operating method performed by a data processing device, according to an embodiment.

Referring to FIG. 7, in operation 710, the data processing device 100 may receive, from the scanner 200, scan data obtained by scanning an object, in real time.

In operation 720, to display, on a display in real time, a portion of the object currently being scanned, the data processing device 100 may generate three-dimensional data, based on the scan data received from the scanner 200 and display an image corresponding to the generated three-dimensional data on the display in real time.

In operation 730, the data processing device 100 may receive a control signal from the scanner 200. The control signal received from the scanner 200 may include a command in which the scanner 200 instructs the data processing device 100 to perform a data processing function, according to a user input detected through a user interface of the scanner 200.

In operation 740, the data processing device 100 may parse the control signal received from the scanner 200 to determine whether the control signal corresponds to an undo command, a redo command, or a locking command. When it is determined that the control signal received from the scanner 200 corresponds to the undo command, operation 750 may be performed.

In operation 750, according to the undo command, the data processing device 100 may hide a predefined number of frames that are most recently input from among frames constituting the three-dimensional data.

In operation 780, the data processing device 100 may display image corresponding to the adjusted voxel data.

Hereinafter, operations of a data processing device according to an undo command will be described with reference to FIG. 8.

Figure 8:
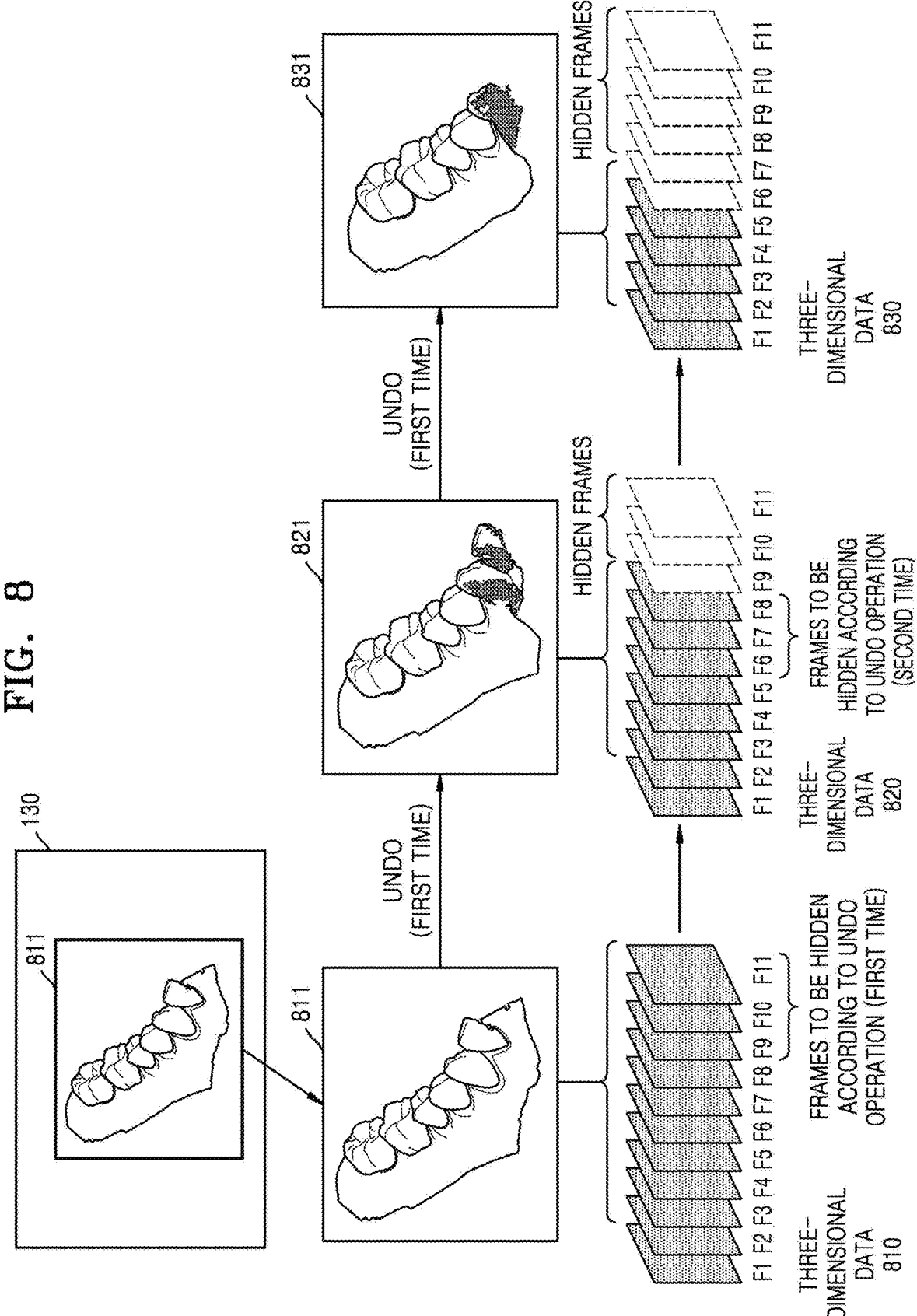
FIG. 8 is a reference diagram for describing a method by which a data processing device operates according to an undo command received from a scanner, according to an embodiment.

FIG. 8 is a reference diagram for describing a method by which a data processing device operates according to an undo command received from a scanner, according to an embodiment.

Referring to FIG. 8, the data processing device 100 may generate three-dimensional data, based on scan data received from the scanner 200, and display an image 811 corresponding to three-dimensional data 810 on the display 130 in real time. The three-dimensional data 810 may include a plurality of frames. For example, the three-dimensional data 810 may include frames F1 to F11. The data processing device 100 may display, on the display 130, the image 811 corresponding to the three-dimensional data 810 including the frames F1 to F11. While the image 811 is displayed on the display 130 of the data processing device 100 as such, a user may wish to hide data that is most recently scanned due to various purposes or reasons. In this case, it is not hygienic and not efficient for a scan operation for the user to input using an input device of the data processing device 100 to hide the data displayed on the display 130 of the data processing device 100 while holding the scanner 200 to scan an oral cavity of a patient. Accordingly, the user may issue a data processing command through a user input by using a user interface provided in the scanner 200. For example, when the user inputs a user input corresponding to an undo command to the scanner 200 while the image 811 is displayed on the display 130 of the data processing device 100, the user input is provided to the data processing device 100, and the data processing device 100 may hide a predefined number of frames from among frames constituting the generated three-dimensional data 810, according to the undo command. For example, when the predefined number of frames to be hidden is three, the data processing device 100 may obtain three-dimensional data 820 by hiding the frames F9, F10, and F11 that are most recently input from among the frames of the three-dimensional data 810, and display, on the display 130, an image 821 corresponding to the three-dimensional data 820 in which the frames F9, F10, and F11 are hidden. When a user input corresponding to a second undo of the user is received from the scanner 200 again while the image 821 is displayed on the display 130 according to a hiding operation, the data processing device 100 may obtain three-dimensional data 830 by hiding the predefined number of frames, for example, three frames F6, F7, and F8, from the three-dimensional data 820, and display, on the display 130, an image 831 corresponding to the three-dimensional data 830 in which total six frames, i.e., the frames F9, F10, and F11 as well as the frames F6, F7, and F8, are hidden.

Hiding according to such an undo command does not display some of frames constituting three-dimensional data to be invisible to a user, and is different from deleting a frame. Thus, the user may display hidden frames again according to a redo command.

According to an embodiment, three-dimensional data to be hidden by the data processing device 100 according to an undo command may include voxel data or mesh data generated based on scan data.

According to an embodiment, a predefined number of frames to be hidden from three-dimensional data by the data processing device 100 according to an undo command may be variously determined.

According to an embodiment, a user input corresponding to an undo command may be received according to an operation of continuously pushing a button provided on the scanner 200 or an operation of continuously shaking the scanner 200, and the data processing device 100 may receive a control signal corresponding to the operation of continuously pushing the button from the scanner 200. In this case, the data processing device 100 may hide frames that are most recently input from three-dimensional data continuously until a button pushing operation is released, and stop a hiding operation when the button pushing operation is released.

According to an embodiment, the data processing device 100 may receive, from the scanner 200, time information of a user pushing the button provided in the scanner 200 and determine the number of frames to be hidden from three-dimensional data in proportion to a time during which the button is pushed. For example, when the time during which the button is pushed is short, the data processing device 100 may hide a small number of frames, and when the time during which the button is pushed is long, the data processing device 100 may hide a large number of frames.

Referring back to FIG. 7, when it is determined that the control signal received from the scanner 200 corresponds to a redo command in operation 740, operation 760 may be performed.

In operation 760, according to the redo command, the data processing device 100 may restore a predefined number of frames that are most recently hidden from among the frames constituting the three-dimensional data.

Hereinafter, operations of a data processing device according to a redo command will be described with reference to FIG. 9.

Figure 9:
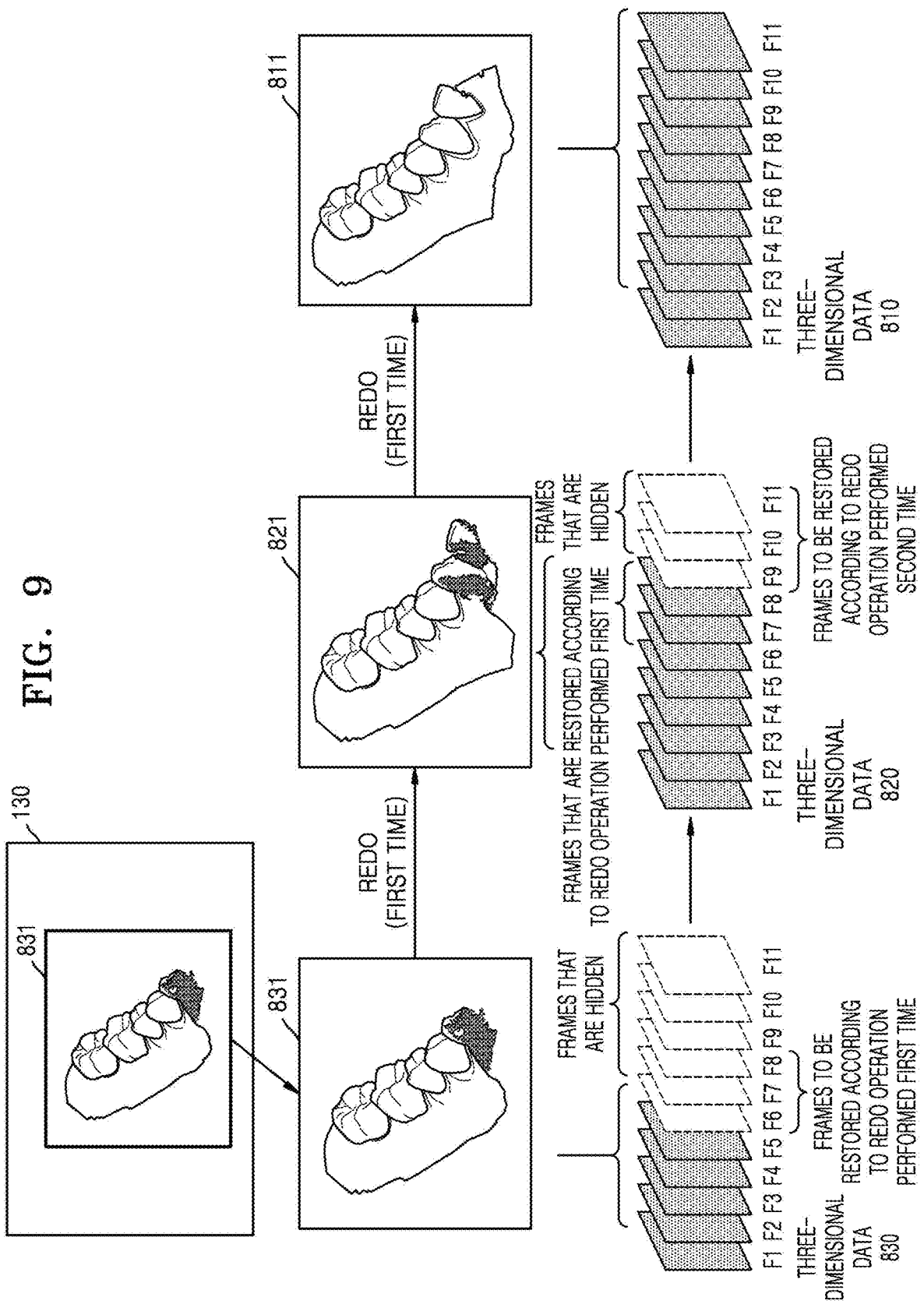
FIG. 9 is a reference diagram for describing a method by which a data processing device operates according to a redo command received from a scanner, according to an embodiment.

FIG. 9 is a reference diagram for describing a method by which a data processing device operates according to a redo command received from a scanner, according to an embodiment.

Referring to FIG. 9, the data processing device 100 may display, on the display 130, the image 831 corresponding to the three-dimensional data 830 in which the frames F6 to F11 are hidden according to the undo operation performed a second time as shown in FIG. 8.

While the image 831 is displayed on the display 130 of the data processing device 100 as such, the user may wish to restore portions that is most recently hidden due to various purposes or reasons. In this case, it is not hygienic and not efficient for the scan operation to input using the input device of the data processing device 100 to restore hidden data while the scanner 200 is held to scan the oral cavity of the patient. Accordingly, the user may issue a data processing command through a user input by using the user interface provided in the scanner 200. For example, when the user inputs a user input corresponding to a redo command to the scanner 200 while the image 831 is displayed on the display 130 of the data processing device 100, the user input is provided to the data processing device 100, and the data processing device 100 may restore a predefined number of frames among hidden frames from among the frames constituting the three-dimensional data 830, according to the redo command. For example, when the predefined number of frames to be restored is three, the data processing device 100 may obtain the three-dimensional data 820 by restoring the frames F6, F7, and F8 that are most recently hidden from among the frames of the three-dimensional data 830, and display, on the display 130, the image 821 corresponding to the three-dimensional data 820 in which the frames F6, F7, and F8 are restored. When a user input corresponding to a second redo of the user is received from the scanner 200 again while the image 821 is displayed on the display 130 according to a restoring operation, the data processing device 100 may obtain the three-dimensional data 810 by restoring the frames F9, F10, and F11 that are most recently hidden from the three-dimensional data 820, and display, on the display 130, the image 811 corresponding to the three-dimensional data 810 in which total six frames, i.e., the frames F6, F7, and F8 as well as the frames F9, F10, and F11, are restored.

According to an embodiment, three-dimensional data to be restored by the data processing device 100 according to a redo command may include voxel data or mesh data generated based on scan data.

According to an embodiment, a predefined number of frames to be restored from three-dimensional data by the data processing device 100 according to a redo command may be variously determined.

According to an embodiment, a user input corresponding to a redo command may be received according to an operation of continuously pushing a button provided on the scanner 200 or an operation of continuously shaking the scanner 200, and the data processing device 100 may receive a control signal corresponding to the operation of continuously pushing the button from the scanner 200. In this case, the data processing device 100 may restore frames that are most recently hidden from three-dimensional data continuously until a button pushing operation is released, and stop the restoring operation when the button pushing operation is released.

According to an embodiment, the data processing device 100 may receive, from the scanner 200, time information of a user pushing the button provided in the scanner 200 and determine the number of frames to be restored from three-dimensional data in proportion to a time during which the button is pushed. For example, when the time during which the button is pushed is short, the data processing device 100 may restore a small number of frames, and when the time during which the button is pushed is long, the data processing device 100 may restore a large number of frames.

Referring back to FIG. 7, when it is determined that the control signal received from the scanner 200 corresponds to a locking command in operation 740, operation 770 may be performed.

In operation 770, the data processing device 100 may finalize the three-dimensional data in a current state such that the three-dimensional data is no longer hidden or restored, according to the locking command.

Hereinafter, operations of a data processing device according to a locking command will be described with reference to FIG. 10.

Figure 10:
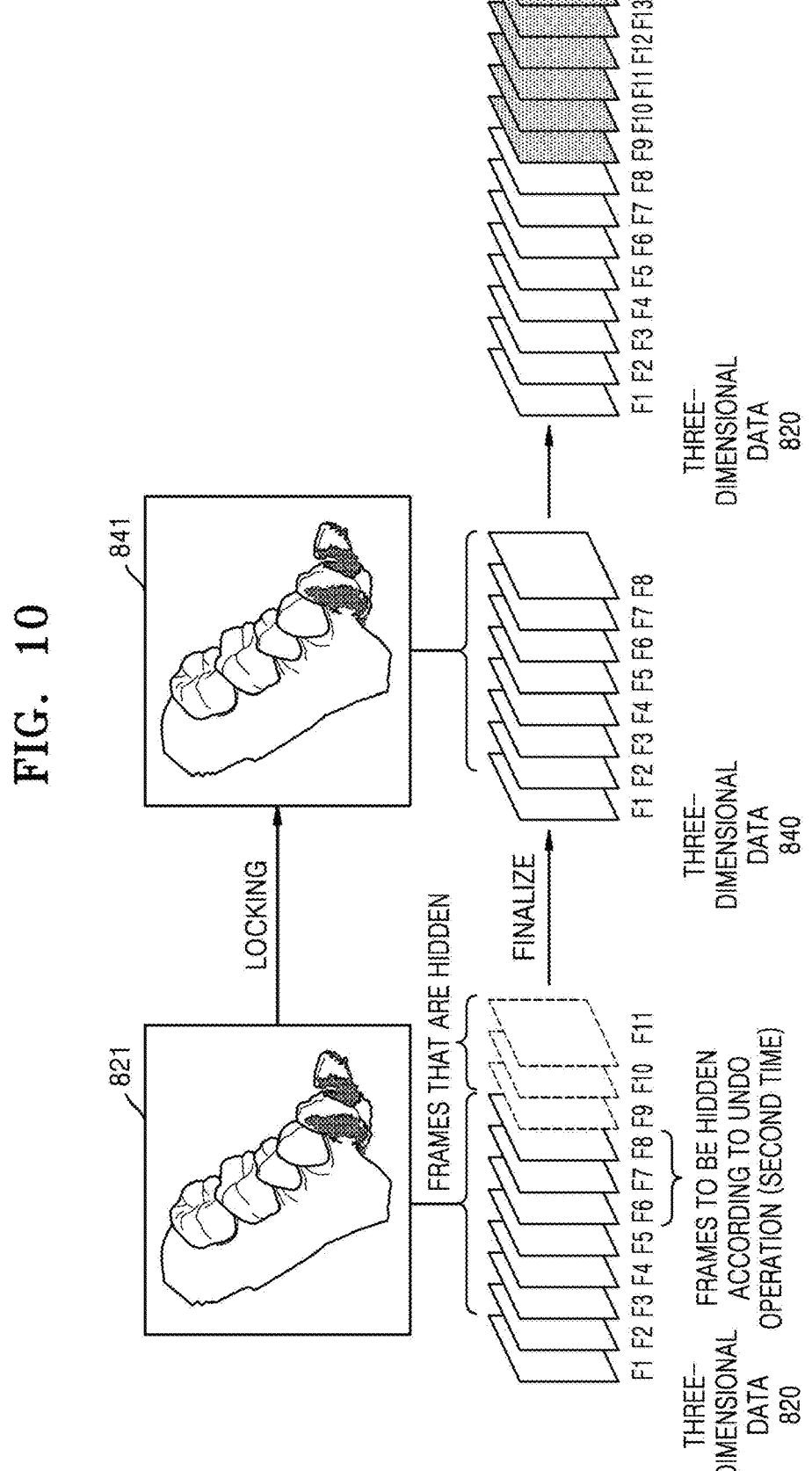
FIG. 10 is a reference diagram for describing a method by which a data processing device operates according to a locking command received from a scanner, according to an embodiment.

FIG. 10 is a reference diagram for describing a method by which a data processing device operates according to a locking command received from a scanner, according to an embodiment.

Referring to FIG. 10, the data processing device 100 may display, on the display 130, the image 821 corresponding to the three-dimensional data 820 in which the frames F9 to F11 are hidden according to the undo operation performed a first time as shown in FIG. 8.

While the image 821 is displayed on the display 130 of the data processing device 100 as such, the user may wish to finalize an image of a current state so that hiding or restoring is no longer performed. For example, the user may wish to no longer modify data in a current state and definitively fix the data in the current state after attempting an undo operation and a redo operation. In this case, it is not be hygienic and not efficient for the scan operation to input using the input device of the data processing device 100 to finalize data while the scanner 200 is held to scan the oral cavity of the patient. Accordingly, the user may issue a data processing command through a user input by using the user interface provided in the scanner 200. For example, when the user inputs a user input corresponding to a locking command to the scanner 200 while the image 821 is displayed on the display 130 of the data processing device 100, the user input is provided to the data processing device 100, and the data processing device 100 may delete the frames F9 to F11 that are hidden from among the frames constituting the three-dimensional data 820, according to the locking command. According to such deleting, the data processing device 100 may generate three-dimensional data 840 including the frames F1 to F8 and display an image 841 corresponding to the three-dimensional data 840. The image 821 and the image 841 are the same, but because the image 841 is an image after locking in which editing is no longer allowed, the user is no longer able to apply an undo function or a redo function on the image 841.

According to an embodiment, the data processing device 100 is unable to apply an undo function or a redo function on three-dimensional data finalized by a locking operation, but is able to apply an undo function or a redo function on three-dimensional data generated based on scan data newly received after the locking. In an example shown in FIG. 10, when the three-dimensional data 840 including the frames F1 to F8 is finalized according to the locking function, and then scan data is received and three-dimensional data 850 is generated by receiving three-dimensional data including new frames F9 to F14, the data processing device 100 may apply an undo function and a redo function on the frames F9 to F14 newly generated after the locking operation.

Generally, when the scanner 200 obtains scan data of an oral cavity by scanning while moving along teeth in the oral cavity that is an object, the data processing device 100 may generate three-dimensional data by aligning frames, based on redundant regions in the scan data. Meanwhile, the user may scan a discontinuous region of the oral cavity by using the scanner 200. For example, when scanning starts from a left molar but moves to a right molar in the middle, the scanner 200 may obtain scan data for two discontinuous regions. An example in which the data processing device 100 performs an undo operation or a redo operation while pieces of three-dimensional data of one or more regions of an object are simultaneously displayed on a display will be described with reference to FIGS. 11 to 13.

Figure 11:
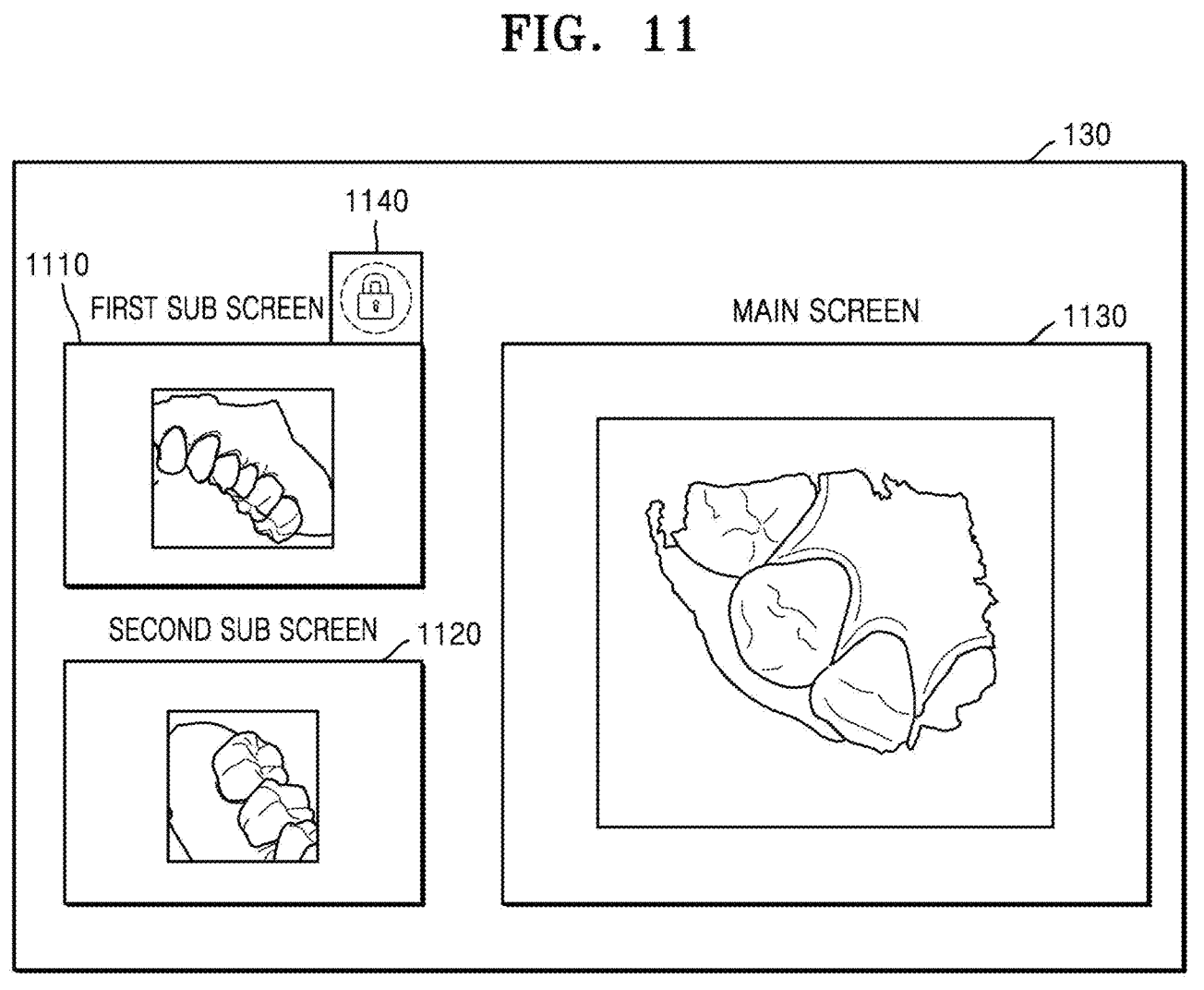

FIG. 11 is a reference diagram for describing an operation by which a data processing device displays an image corresponding to a plurality of regions of an object, according to an embodiment.

Referring to FIG. 11, the data processing device 100 may display a thumbnail of a first image corresponding to a first region of an object on a first sub screen 1110, display a thumbnail of a second image corresponding to a second region spaced apart from the first region of the object on a second sub screen 1120, and display a third image corresponding to a third region spaced apart from the first region or second region of the object on a main screen 1130. The number of sub screens may be variously determined.

According to an embodiment, the data processing device 100 may perform a data processing operation, such as an undo, a redo, or a locking, on three-dimensional data corresponding to an image displayed on a main screen. Accordingly, to perform the data processing operation on an image displayed on a sub screen, an image corresponding to the sub screen may be moved to the main screen. A user may switch the image displayed on the main screen with an image displayed on a first sub screen or a second sub screen, according to a user input. For example, the user may display, on the main screen, a first image corresponding to a thumbnail displayed on the first sub screen, according to an operation of dragging the thumbnail displayed on the first sub screen to the main screen, and a thumbnail of a third image displayed on the main screen may be displayed on the first sub screen. After the movement as such, the data processing device 100 may perform the data processing operation on the third image displayed on the main screen 1130.

According to an embodiment, when the image displayed on the main screen is all hidden according to repeated undo operations and thus there is no image to be displayed, the data processing device 100 may not perform any operation. In this case, the user may manually move an image displayed on a sub screen to the main screen.

According to an embodiment, when the image displayed on the main screen is all hidden according to repeated undo operations and thus there is no image to be displayed, the data processing device 100 may automatically move the image corresponding to the sub screen to the main screen and display the image. Here, the data processing device 100 may move the image corresponding to the sub screen to the main screen in the order from most recently scanned data. For example, when the image of the second sub screen is more recently scanned data, the data processing device 100 may move the image corresponding to the second sub screen to the main screen.

According to an embodiment, the data processing device 100 may set locking for each sub screen. The locking may denote a setting that disables an undo operation or a redo operation. Referring to FIG. 11, a lock icon 1140 indicating locking is displayed on the first sub screen 1110. The locking may be indicated not only by a lock icon, but also by a visual effect using a color or thickness of an edge of a sub screen.

Figure 12:
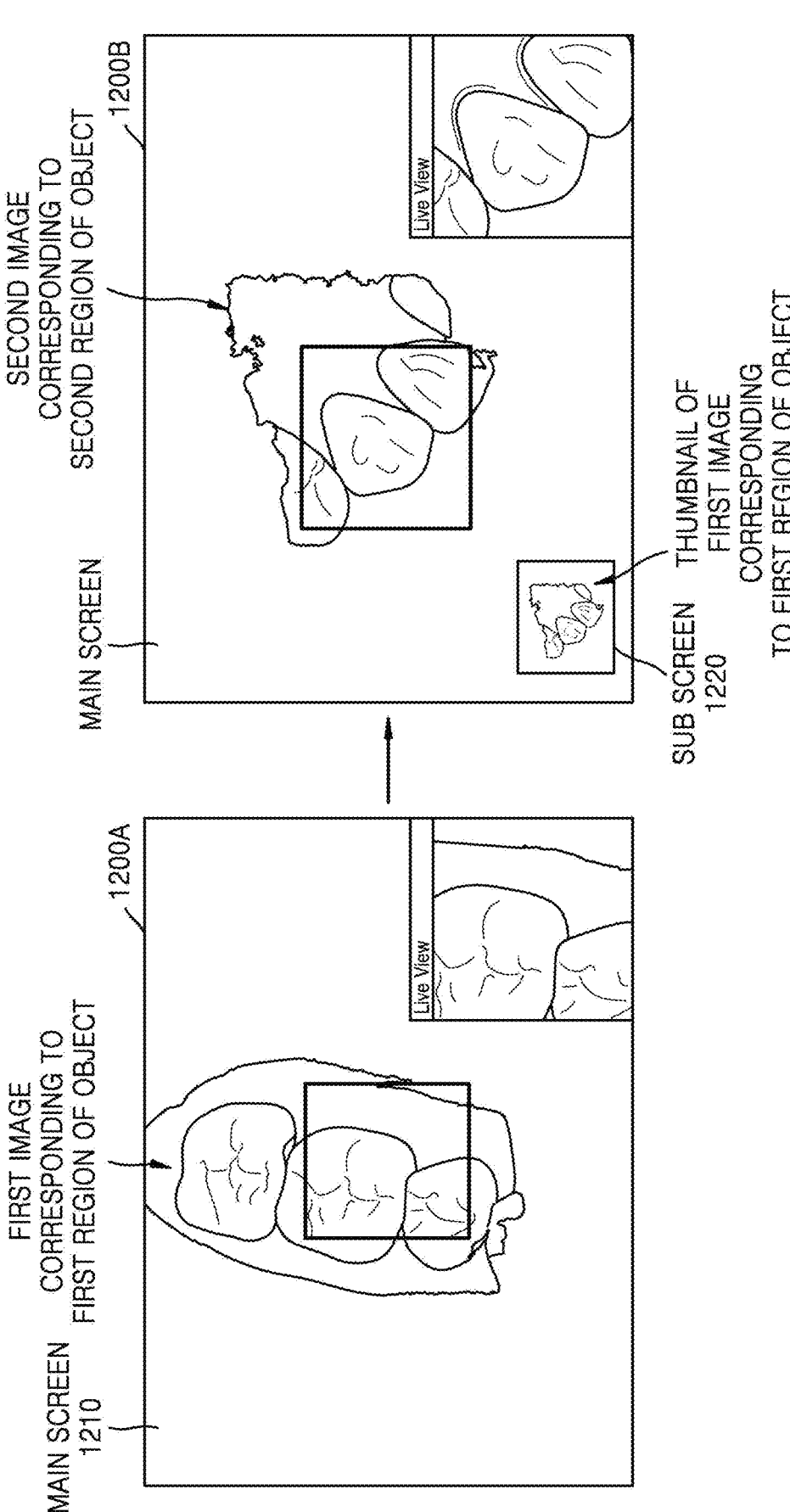
FIG. 12 is a reference diagram for describing an operation of displaying, on a display of a data processing device, three-dimensional data corresponding to a first region of an object, according to an embodiment.

FIG. 12 is a reference diagram for describing an operation of displaying, on a display of a data processing device, three-dimensional data corresponding to a first region of an object, according to an embodiment.

Referring to FIG. 12, the data processing device 100 may receive scan data corresponding to a first region of an oral cavity that is an object, generate three-dimensional data by processing the received scan data, and display a first image corresponding to the generated three-dimensional data on a main screen 1210 of a display in real time.

Then, upon receiving scan data corresponding to a second region that is not continuous from the first region, i.e., spaced apart from the first region, the data processing device 100 may display a thumbnail image of the first image corresponding to the first region to a sub screen 1220, generate three-dimensional data by processing the scan data corresponding to the second region, and display a second image corresponding to the generated three-dimensional data on the main screen 1210 of the display in real time.

While images corresponding to different regions are displayed on the main screen 1210 and the sub screen 1220 of the display of the data processing device 100 as such, a user may perform an undo operation or a redo operation on the image displayed on the main screen 1210, i.e., the second image corresponding to the second region. In other words, when a user input corresponding to the undo operation is input as the user manipulates the scanner 200 while the images corresponding to different regions are displayed on the main screen 1210 and the sub screen 1220 as in 1200B of FIG. 12, the data processing device 100 may receive a control signal corresponding to the user input from the scanner 200 and perform hiding on the three-dimensional data corresponding to the second image corresponding to the second region displayed on the main screen 1210. Also, when the user repeatedly performs the undo operation on the second image corresponding to the second region displayed on the main screen 1210 and all the second image displayed on the main screen 1210 is hidden and thus there is no second image to be displayed on the main screen 1210, the data processing device 100 may operate according to various scenarios.

According to an embodiment, when the user repeatedly performs the undo operation on the second image corresponding to the second region displayed on the main screen 1210 and all the second image displayed on the main screen 1210 is hidden and thus there is no second image to be displayed on the main screen 1210, the data processing device 100 may not perform any operation automatically. In other words, the data processing device 100 performs a data processing operation, i.e., an undo operation, a redo operation, or a locking operation, on three-dimensional data corresponding to an image displayed on the main screen 1210, and thus the user needs to move an image of the sub screen 1220 to the main screen 1210 to perform the data processing operation on an image of the sub screen 1220. For example, the user may enable the first image corresponding to the sub screen 1220 to be displayed on the main screen 1210 through a user input such as an operation of dragging the thumbnail of the first image displayed on the sub screen 1220 to the main screen 1210. Then, when the user inputs a user input corresponding to the undo operation by manipulating the scanner 200 while the first image is displayed on the main screen 1210 as such, the data processing device 100 may receive a control signal corresponding to the user input from the scanner 200 and perform hiding on the three-dimensional data of the first image corresponding to the main screen 1210 according to the reception of the control signal.

According to an embodiment, when the user wishes to perform the data processing operation on the first image displayed on the sub screen 1220 while the second image is displayed on the main screen 1210 and the first image is displayed on the sub screen 1220 of the display of the data processing device 100, the user may switch positions of the second image displayed on the main screen 1210 and the first image displayed on the sub screen 1220 and perform the data processing operation on the first image while the first image is displayed on the main screen 1210.

According to an embodiment, when the user repeatedly performs the undo operation on the second image corresponding to the second region displayed on the main screen 1210 as in 1200B of FIG. 12, and all the second image displayed on the main screen 1210 is hidden and thus there is no second image to be displayed on the main screen 1210, the data processing device 100 may automatically move the image of the sub screen 1220 to the main screen 1210.

Figure 13:
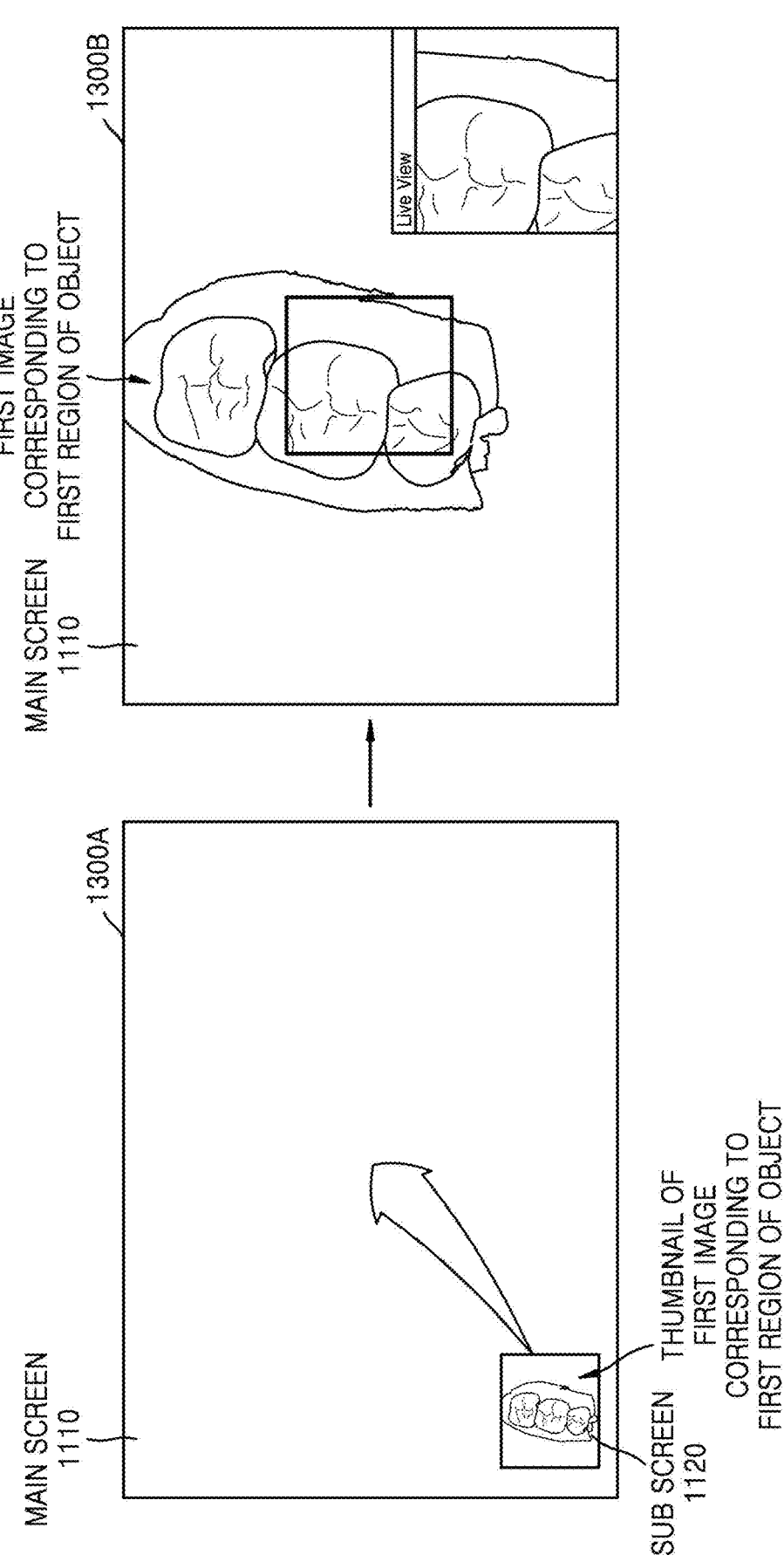
FIG. 13 is a reference diagram for describing an operation by which a data processing device automatically moves an image of a sub screen to a main screen when images displayed on the main screen are all hidden.

FIG. 13 is a reference diagram for describing an operation by which the data processing device 100 automatically moves the image of the sub screen 1220 to the main screen 1210 when the image displayed on the main screen 1210 is all hidden.

Referring to 1300A of FIG. 13, when the undo operation is repeatedly performed on the second image corresponding to the second region displayed on the main screen 1210, and all the second image displayed on the main screen 1210 is hidden and thus there is no second image to be displayed on the main screen 1210, the data processing device 100 may automatically move the first image corresponding to the thumbnail displayed on the sub screen 1220 to the main screen 1210. Then, when a control signal corresponding to a user input instructing an undo operation is received, the data processing device 100 may perform hiding on the three-dimensional data corresponding to the first image displayed on the main screen 1210.

An intraoral image processing method according to an embodiment of the present disclosure may be recorded on a computer-readable recording medium by being implemented in the form of program commands executed by using various computers. Also, an embodiment of the present disclosure may include a computer-readable storage medium having recorded thereon at least one program including at least one instruction for executing the intraoral image processing method.

The computer-readable recording medium may include at least one of a program command, a data file, or a data structure. Examples of the computer-readable recording medium include magnetic media such as hard disks, floppy disks, and magnetic tapes, optical media such as CD-ROMs and DVDs, magneto-optical media such as floptical disks, and hardware devices configured to store and perform program commands, such as read-only memory (ROM), random-access memory (RAM), and flash memory.

A machine-readable storage medium may be provided in the form of a non-transitory storage medium. The "non-transitory storage medium" may denote that a storage medium is a tangible device. The "non-transitory storage medium" may include a buffer where data is temporarily stored.

According to an embodiment, an intraoral image processing method according to various embodiments in the present specification may be provided by being included in a computer program product. The computer program product may be distributed in the form of the machine-readable storage medium (e.g., a compact disc read-only memory (CD-ROM). Alternatively, the computer program product may be distributed (e.g., downloaded or uploaded) directly or online through an application store (e.g., PlayStore™) or between two user devices (e.g., smartphones). In detail, the computer program product according to an embodiment may include a storage medium having recorded thereon a program including at least one instruction for executing the intraoral image processing method according to an embodiment.

While the embodiments have been particularly shown and described in detail, it will be understood by one of ordinary skill in the art that various changes in form and details may be made therein without departing from the spirit and scope of the present disclosure as defined by the following claims.

Some embodiment may also be realized in the form of a recording medium including instructions executable by a computer, such as a program module executed by a computer. A computer-readable medium may be an arbitrary available medium accessible by a computer, and includes all volatile and non-volatile media and separable and non-separable media. Further, the computer-readable recording medium may include a computer storage medium. Examples of the computer storage medium include all volatile and non-volatile media and separable and non-separable media, which have been implemented by an arbitrary method or technology, for storing information such as computer-readable instructions, data structures, program modules, and other data.

The embodiments may be implemented as a software program that includes instructions stored on computer-readable storage media.

A computer is an apparatus capable of calling a stored instruction from a storage medium and operating according to the embodiment according to the called instruction, and may include an electronic device according to the embodiments.

The computer-readable storage medium may be provided in the form of a non-transitory storage medium. The term "non-transitory" only means that a storage medium does not include a signal and is tangible, and does not distinguish whether data is stored in the storage medium semi-permanently or temporarily.

Furthermore, a control method according to the embodiments may be provided by being included in a computer program product. The computer program products are products that can be traded between sellers and buyers.

The computer program product may include a software program or a computer-readable storage medium storing a software program. For example, the computer program product may include a product (for example, a downloadable application) in a form of a software program that is electronically distributable through a manufacturer of a device or an electronic market (for example, Google Play-Store™ or AppStore™). For electronic distribution, at least a part of the software program may be stored in the storage medium or temporarily generated. In this case, the storage medium may be a storage medium of a server of a manufacturer, a server of an electronic market, or a relay server that temporarily stores the software program.

The computer program product may include a storage medium of a server or a storage medium of a device, in a system including the server and the device. Alternatively, when there is a third device (e.g., a smartphone) that communicates with a server or a device, the computer program product may include a storage medium of the third device. Alternatively, the computer program product may include the software program transmitted from the server to the device or the third device, or transmitted from the third device to the device.

In this case, one of the server, the device, and the third device may perform a method according to the embodiments by executing the computer program product. Alternatively, two or more of the server, the device, and the third device may perform the method according to the embodiments in a distributed fashion by executing the computer program product.

For example, a server, for example, a cloud server or an artificial intelligence server, may execute the computer program product stored in the server to control the device communicatively connected to the server to perform the method according to the embodiments.

In another example, the third device may execute the computer program product to control the device communicatively connected to the third device to perform the method according to the embodiment. When the third device executes the computer program product, the third device may download the computer program product from the server and execute the downloaded computer program product. Alternatively, the third device may execute a computer program product provided in a preloaded state to perform the method according to the embodiments.

Furthermore, in the specification, the term "unit" may be a hardware component such as a processor or circuit and/or a software component that is executed by a hardware component such as a processor.

The above description of the present disclosure is provided for illustration, and it will be understood by one of ordinary skill in the art that various changes in form and details may be readily made therein without departing from essential features and the scope of the present disclosure as defined by the following claims. Accordingly, the embodiments described above are examples in all aspects and are not limited. For example, each element described as a single type may be implemented in a distributed manner, and similarly, elements described as distributed may be implemented in a combined form.

The scope of the present disclosure is defined by the appended claims rather than the detailed description, and all changes or modifications within the scope of the appended claims and their equivalents will be construed as being included in the scope of the present disclosure.

The invention claimed is:

1. A data processing device comprising:
a display;
a communication interface;
a memory storing one or more instructions; and
a processor configured to execute the one or more instructions to:
control the communication interface to receive, from a scanner, scan data of an object obtained by scanning the object;
control the display to display an image corresponding to three-dimensional data generated based on the scan data;
control the communication interface to receive, from the scanner, a control signal generated according to a user input detected through one or more user interfaces of the scanner, while the image is displayed;
obtain adjusted three-dimensional data which is adjusted based on frames excluding one or more frames which are hidden among the frames, by hiding one or more frames among the frames forming the three-dimensional data, based on the control signal, or obtain the adjusted three-dimensional data which is adjusted based on frames including one or more frames which are restored, by restoring the one or more hidden frames, based on the control signal; and
control the display to display the image, based on the adjusted three-dimensional data.

2. The data processing device of claim 1, wherein the processor is further configured to execute the one or more instructions to:

based on the control signal corresponding to an undo command, hide a predefined number of frames that are most recently input from among frames constituting the three-dimensional data.

3. The data processing device of claim 2, wherein the processor is further configured to execute the one or more instructions to:

based on the control signal corresponding to a redo command, restore the predefined number of frames that are most recently hidden.

4. The data processing device of claim 3, wherein the processor is further configured to execute the one or more instructions to:

based on the control signal corresponding to a locking command, finalize the three-dimensional data, based on the three-dimensional data in a current state, such that the hiding or restoring is no longer allowed.

5. The data processing device of claim 1, wherein the processor is further configured to execute the one or more instructions to:

control the display to display, on a sub screen, a first image corresponding to first three-dimensional data generated based on scan data corresponding to a first region of the object;

control the display to display, on a main screen, a second image corresponding to second three-dimensional data generated based on scan data corresponding to a second region of the object, the second region being spaced apart from the first region;

perform a function of adjusting the second three-dimensional data corresponding to the second image displayed on the main screen, according to a control signal received from the scanner; and control the display to display the second image, based on the adjusted second three-dimensional data.

6. The data processing device of claim 5, wherein the processor is further configured to execute the one or more instructions to set a locking function on the first three-dimensional data corresponding to the first image displayed on the sub screen, the locking function ensuring that a data adjustment function is not performed.

7. The data processing device of claim 5, wherein the processor is further configured to execute the one or more instructions to:

when all pieces of the second three-dimensional data are hidden according to an operation of hiding a predefined number of frames that are most recently input from among frames constituting the second three-dimensional data, based on the control signal corresponding to an undo command, control the display to display, on the main screen, the first image corresponding to the first three-dimensional data, the first image corresponding to the sub screen.

8. An operating method of a data processing device, the operating method comprising:

receiving, from a scanner, scan data of an object obtained by scanning the object;

displaying an image corresponding to three-dimensional data generated based on the scan data;

while the image is displayed, receiving, from the scanner, a control signal generated according to a user input detected through one or more user interfaces of the scanner;

obtaining adjusted three-dimensional data which is adjusted based on frames excluding one or more frames which are hidden among the frames, by hiding one or more frames among the frames forming the three-dimensional data, based on the control signal, or obtaining the adjusted three-dimensional data which is adjusted based on frames including one or more frames which are restored, by restoring the one or more hidden frames, based on the control signal; and displaying the image, based on the adjusted three-dimensional data.

9. The operating method of claim 8, further comprising, based on the control signal corresponding to an undo command, hiding a predefined number of frames that are most recently input from among frames constituting the three-dimensional data.

10. The operating method of claim 9, further comprising, based on the control signal corresponding to a redo command, restoring the predefined number of frames that are most recently hidden.

11. The operating method of claim 10, further comprising, based on the control signal corresponding to a locking command, finalizing the three-dimensional data, based on the three-dimensional data in a current state, such that the hiding or the restoring is no longer allowed.

12. The operating method of claim 8, further comprising:

displaying, on a sub screen, a first image corresponding to first three-dimensional data generated based on scan data corresponding to a first region of the object;

displaying, on a main screen, a second image corresponding to second three-dimensional data generated based on scan data corresponding to a second region of the object, the second region being spaced apart from the first region;

performing a function of adjusting the second three-dimensional data corresponding to the second image displayed on the main screen, according to a control signal received from the scanner; and displaying the second image, based on the adjusted second three-dimensional data.

13. The operating method of claim 12, further comprising setting a locking function on the first three-dimensional data corresponding to the first image displayed on the sub screen, the locking function ensuring that a data adjustment function is not performed.

14. The operating method of claim 12, further comprising, when all pieces of the second three-dimensional data are hidden according to an operation of hiding a predefined number of frames that are most recently input from among frames constituting the second three-dimensional data, based on the control signal corresponding to an undo command, displaying, on the main screen, the first image corresponding to the first three-dimensional data, the first image corresponding to the sub screen.

15. A computer-readable recording medium having recorded thereon one or more programs executed by a processor of a data processing device to implement an operating method of the data processing device, wherein the operating method of the data processing device comprises:

receiving, from a scanner, scan data of an object obtained by scanning the object;

displaying an image corresponding to three-dimensional data generated based on the scan data;

receiving, from the scanner, a control signal generated according to a user input detected through one or more user interfaces of the scanner, while the image is displayed;

obtaining adjusted three-dimensional data which is adjusted based on frames excluding one or more frames which are hidden among the frames, by hiding one or more frames among the frames forming the three-dimensional data, based on the control signal, or obtaining the adjusted three-dimensional data which is adjusted based on frames including one or more frames which are restored, by restoring the one or more hidden frames, based on the control signal; and displaying the image, based on the adjusted three-dimensional data.

* * * * *